(12) United States Patent
Flaherty

(10) Patent No.: US 8,060,194 B2
(45) Date of Patent: Nov. 15, 2011

(54) BIOLOGICAL INTERFACE SYSTEM WITH AUTOMATED CONFIGURATION

(75) Inventor: J. Christopher Flaherty, Topsfield, MA (US)

(73) Assignee: BrainGate Co., LLC, Ponte Vedra Beach, FL (US)

(*) Notice: Subject to any disclaimer, the term of this patent is extended or adjusted under 35 U.S.C. 154(b) by 1527 days.

(21) Appl. No.: 11/320,709

(22) Filed: Dec. 30, 2005

(65) Prior Publication Data

US 2006/0189900 A1    Aug. 24, 2006

Related U.S. Application Data

(60) Provisional application No. 60/644,686, filed on Jan. 18, 2005.

(51) Int. Cl.
*A61B 5/04* (2006.01)

(52) U.S. Cl. .................. 600/544; 600/545

(58) Field of Classification Search .......... 600/544–545
See application file for complete search history.

(56) References Cited

U.S. PATENT DOCUMENTS

| | | | |
|---|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,566,464 A | 1/1986 | Piccone et al. |
| 4,633,889 A | 1/1987 | Talalla et al. |
| 4,690,142 A | 9/1987 | Ross et al. |
| 4,837,049 A | 6/1989 | Byers et al. |
| 4,865,048 A | 9/1989 | Eckerson |
| 4,878,913 A | 11/1989 | Aebischer et al. |
| 4,883,666 A | 11/1989 | Sabel et al. |
| 4,969,468 A | 11/1990 | Byers et al. |
| 5,037,376 A | 8/1991 | Richmond et al. |
| 5,081,990 A | 1/1992 | Deletis |
| 5,092,329 A | 3/1992 | Graupe et al. |
| 5,119,832 A | 6/1992 | Xavier |
| 5,156,844 A | 10/1992 | Aebischer et al. |

(Continued)

FOREIGN PATENT DOCUMENTS

EP    0 911 061 A    4/1999

(Continued)

OTHER PUBLICATIONS

Pfurtscheller, G. et al., "Motor Imagery and Direct Brain-Computer Communication," Proceedings of the IEEE, vol. 89, No. 7, Jul. 2001.

(Continued)

*Primary Examiner* — Patricia Mallari
*Assistant Examiner* — Michael D'Angelo
(74) *Attorney, Agent, or Firm* — SoCal IP Law Group LLP; Steven C. Sereboff; M. Kala Sarvaiya

(57) ABSTRACT

A system and method for a biological interface system that processes multicellular signals of a patient and controls one or more devices is disclosed. The system includes a sensor that detects the multicellular signals and a processing unit for producing the control signal based on the multicellular signals. The system further includes an automated configuration routine that is used to set or modify the value of one or more system configuration parameters.

9 Claims, 6 Drawing Sheets

U.S. PATENT DOCUMENTS

| | | |
|---|---|---|
| 5,215,088 A | 6/1993 | Normann et al. |
| 5,325,862 A | 7/1994 | Lewis et al. |
| 5,325,865 A | 7/1994 | Beckman et al. |
| 5,361,760 A | 11/1994 | Normann et al. |
| 5,423,877 A | 6/1995 | Mackey |
| 5,445,608 A | 8/1995 | Chen et al. |
| 5,458,631 A | 10/1995 | Xavier |
| 5,474,547 A | 12/1995 | Aebischer et al. |
| 5,476,441 A | 12/1995 | Durfee et al. |
| 5,549,656 A | 8/1996 | Reiss |
| 5,617,871 A | 4/1997 | Burrows |
| 5,638,826 A | 6/1997 | Wolpaw et al. |
| 5,687,291 A | 11/1997 | Smyth |
| 5,692,517 A | 12/1997 | Junker |
| 5,697,951 A | 12/1997 | Harpstead et al. |
| 5,702,432 A | 12/1997 | Chen et al. |
| 5,713,923 A | 2/1998 | Ward et al. |
| 5,724,987 A | 3/1998 | Gevins et al. |
| 5,735,885 A | 4/1998 | Howard, III et al. |
| 5,758,651 A | 6/1998 | Nygard et al. |
| 5,797,898 A | 8/1998 | Santini, Jr. et al. |
| 5,814,089 A | 9/1998 | Stokes et al. |
| 5,843,093 A | 12/1998 | Howard, III |
| 5,843,142 A | 12/1998 | Sultan |
| 5,855,801 A | 1/1999 | Lin et al. |
| 5,857,978 A | 1/1999 | Hively et al. |
| 5,873,840 A | 2/1999 | Neff |
| 5,928,228 A | 7/1999 | Kordis et al. |
| 5,938,688 A | 8/1999 | Schiff |
| 5,938,689 A | 8/1999 | Fischell et al. |
| 5,938,690 A | 8/1999 | Law et al. |
| 5,995,868 A | 11/1999 | Dorfmeister et al. |
| 6,001,065 A | 12/1999 | DeVito |
| 6,006,124 A | 12/1999 | Fischell et al. |
| 6,016,449 A | 1/2000 | Fischell et al. |
| 6,018,682 A | 1/2000 | Rise et al. |
| 6,024,700 A | 2/2000 | Nemirovski et al. |
| 6,024,702 A | 2/2000 | Iversen |
| 6,027,456 A | 2/2000 | Feler et al. |
| 6,038,477 A | 3/2000 | Kayyali |
| 6,044,292 A | 3/2000 | Heyrend et al. |
| 6,061,593 A | 5/2000 | Fischell et al. |
| 6,086,582 A | 7/2000 | Altman et al. |
| 6,091,015 A | 7/2000 | del Valle et al. |
| 6,092,058 A | 7/2000 | Smyth |
| 6,094,598 A | 7/2000 | Elsberry et al. |
| 6,113,553 A | 9/2000 | Chubbuck |
| 6,125,300 A | 9/2000 | Weijand et al. |
| 6,128,538 A | 10/2000 | Fischell et al. |
| 6,134,474 A | 10/2000 | Fischell et al. |
| 6,154,678 A | 11/2000 | Lauro |
| 6,161,045 A | 12/2000 | Fischell et al. |
| 6,163,725 A | 12/2000 | Peckham et al. |
| 6,169,981 B1 | 1/2001 | Werbos |
| 6,171,239 B1 | 1/2001 | Humphrey |
| 6,175,762 B1 | 1/2001 | Kirkup et al. |
| 6,181,965 B1 | 1/2001 | Loeb et al. |
| 6,185,455 B1 | 2/2001 | Loeb et al. |
| 6,216,045 B1 | 4/2001 | Black et al. |
| 6,224,549 B1 | 5/2001 | Drongelen |
| 6,240,315 B1 | 5/2001 | Mo et al. |
| 6,254,536 B1 | 7/2001 | DeVito |
| 6,263,237 B1 | 7/2001 | Rise |
| 6,280,394 B1 | 8/2001 | Maloney et al. |
| 6,304,775 B1 | 10/2001 | Iasemidis et al. |
| 6,309,410 B1 | 10/2001 | Kuzma et al. |
| 6,313,093 B1 | 11/2001 | Frey, II |
| 6,319,241 B1 | 11/2001 | King et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,358,202 B1 | 3/2002 | Arent |
| 6,360,122 B1 | 3/2002 | Fischell et al. |
| 6,366,813 B1 | 4/2002 | DiLorenzo |
| 6,427,086 B1 | 7/2002 | Fischell et al. |
| 6,436,708 B1 | 8/2002 | Leone et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,549,804 B1 | 4/2003 | Osorio et al. |
| 6,577,893 B1 | 6/2003 | Besson et al. |
| 6,620,415 B2 | 9/2003 | Donovan |
| 6,658,287 B1 | 12/2003 | Litt et al. |
| 7,010,351 B2 | 3/2006 | Firlik et al. |
| 7,162,305 B2 | 1/2007 | Tong et al. |
| 7,212,851 B2 | 5/2007 | Donoghue et al. |
| 7,280,870 B2 | 10/2007 | Nurmikko et al. |
| 7,346,396 B2 | 3/2008 | Barriskill et al. |
| 7,381,192 B2 | 6/2008 | Brodard et al. |
| 7,392,079 B2 | 6/2008 | Donoghue et al. |
| 7,647,097 B2 | 1/2010 | Flaherty et al. |
| 2001/0023368 A1 | 9/2001 | Black et al. |
| 2001/0027336 A1 | 10/2001 | Gielen et al. |
| 2001/0029391 A1 | 10/2001 | Gluckman et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0016638 A1 | 2/2002 | Mitra et al. |
| 2002/0077534 A1 | 6/2002 | DuRousseau |
| 2002/0077620 A1 | 6/2002 | Sweeney et al. |
| 2002/0082514 A1 | 6/2002 | Williams et al. |
| 2002/0099412 A1 | 7/2002 | Fischell et al. |
| 2002/0169485 A1 | 11/2002 | Pless et al. |
| 2003/0004428 A1 | 1/2003 | Pless et al. |
| 2003/0074032 A1 | 4/2003 | Gliner |
| 2003/0082507 A1 | 5/2003 | Stypulkowski |
| 2003/0083716 A1 | 5/2003 | Nicolelis et al. |
| 2003/0083724 A1 | 5/2003 | Jog et al. |
| 2003/0093129 A1 | 5/2003 | Nicolelis et al. |
| 2003/0139782 A1 | 7/2003 | Duncan et al. |
| 2003/0139783 A1* | 7/2003 | Kilgore et al. .............. 607/49 |
| 2004/0006264 A1 | 1/2004 | Majarradi et al. |
| 2004/0073414 A1 | 4/2004 | Bienenstock et al. |
| 2004/0138579 A1 | 7/2004 | Deadwyler et al. |
| 2005/0090756 A1 | 4/2005 | Wolf et al. |
| 2005/0137652 A1 | 6/2005 | Cauller et al. |
| 2005/0267597 A1 | 12/2005 | Flaherty et al. |
| 2005/0273890 A1 | 12/2005 | Flaherty et al. |
| 2006/0049957 A1 | 3/2006 | Surgenor et al. |
| 2006/0058627 A1* | 3/2006 | Flaherty et al. ............ 600/409 |
| 2006/0149338 A1 | 7/2006 | Flaherty et al. |
| 2006/0167371 A1 | 7/2006 | Flaherty et al. |
| 2006/0167530 A1 | 7/2006 | Flaherty et al. |
| 2006/0173259 A1 | 8/2006 | Flaherty et al. |
| 2006/0189900 A1 | 8/2006 | Flaherty |
| 2006/0195042 A1 | 8/2006 | Flaherty |
| 2006/0206167 A1 | 9/2006 | Flaherty et al. |
| 2006/0241356 A1 | 10/2006 | Flaherty |
| 2006/0253166 A1 | 11/2006 | Flaherty et al. |
| 2007/0032738 A1 | 2/2007 | Flaherty et al. |
| 2007/0156126 A1 | 7/2007 | Flaherty |
| 2010/0023021 A1 | 1/2010 | Flaherty |
| 2010/0063411 A1 | 3/2010 | Donoghue et al. |

FOREIGN PATENT DOCUMENTS

| | | |
|---|---|---|
| WO | WO 01/43635 | 6/2001 |
| WO | WO 01/60445 | 8/2001 |
| WO | WO 01/78833 | 10/2001 |
| WO | WO 01/93756 A2 | 12/2001 |
| WO | WO 02/093312 A2 | 11/2002 |
| WO | WO 02/100267 A1 | 12/2002 |
| WO | WO 03/035165 | 5/2003 |
| WO | WO 03/037231 | 5/2003 |
| WO | WO 03/061465 A2 | 7/2003 |
| WO | WO 2006/044793 A2 | 4/2006 |

OTHER PUBLICATIONS

Leeb, R. et al., "Walking through a Virtual City by Thought," Proceedings of the 26th Annual International Conference of the IEEE EMBS, San Francisco, CA, USA, Sep. 1-5, 2004.

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electroencephaloraphy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. ½, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data—Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhom et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al, "Neuronal Interactions Improve Cortical Population Coding of Movement Direction," The journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure for Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real—Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter," Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroprosthesis Suitable for Implantation Into the Brain," IEEE Transactions on Neural Systems and Rehabilitation Engineering, vol. 11, No. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering, vol. 3, No. 4, Dec. 1995.

Ferdinando Mussa-Ivaldi et al., "Brain-machine interfaces: computational demands and clinical needs meet basic neuroscience," TRENDS in Neurosciences, vol. 26, No. 6, Jun. 2003, pp. 329-334.

D.N. Harvey et al., "Multiple-Output Electromyographic Switching System," 1978 ISA, Pittsburgh, PA, 1978, pp. 121-123.

Faisal Karmali et al.,"Environmental Control by a Brain-Computer Interface," Proceedings of the 22nd Annual EMBS Int'l Conf., Jul. 23-28, 2000, Chicago, IL, pp. 2990-2992.

Alex Mihailidis et al. "Using artificial intelligence to assist people with dementia to be more independent," Proceedings of the 22nd Annual EMBS Int'l Conf., Jul. 23-28, 2000, Chicago, IL, pp. 2993-2996.

* cited by examiner

BIOLOGICAL INTERFACE SYSTEM WITH AUTOMATED CONFIGURATION

CROSS-REFERENCE TO RELATED APPLICATIONS

This application claims the benefit of priority under 35 U.S.C. §119(e) of U.S. Provisional Application No. 60/644,686, filed Jan. 18, 2005. This application relates to commonly assigned U.S. application Ser. No. 11/321,860 of J. Christopher Flaherty et al., entitled "BIOLOGICAL INTERFACE SYSTEM WITH THRESHOLDED CONFIGURATION" and filed on the same date as the present application. The complete subject matter of the above-referenced applications is incorporated by reference herein.

FIELD OF THE INVENTION

The present invention relates to medical devices and related methods. More particularly, various embodiments relate to biological interface systems that include one or more devices controlled by processed multicellular signals of a patient. A processing unit produces a control signal based on multicellular signals received from a sensor consisting of multiple electrodes. More particularly, the system includes an automated patient training routine that is used to configure the system to optimize control of the devices.

DESCRIPTION OF RELATED ART

Biological interface devices, for example neural interface devices, are currently under development for numerous patient applications including restoration of lost function due to traumatic injury or neurological disease. Sensors, such as electrode arrays, implanted in the higher brain regions that control voluntary movement, can be activated voluntarily to generate electrical signals that can be processed by a biological interface device to create a thought invoked control signal. Such control signals can be used to control numerous devices including computers and communication devices, external prostheses, such as an artificial arm or functional electrical stimulation of paralyzed muscles, as well as robots and other remote control devices. Patients afflicted with amyotrophic lateral sclerosis (Lou Gehrig's Disease), particularly those in advanced stages of the disease, would also be appropriate for receiving a neural interface device, even if just to improve communication to the external world, including Internet access, and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information or other neural data, such as electrocorticogram (ECoG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression will be to more sophisticated human applications, such as those types of devices regulated by various governmental regulatory agencies including the Food and Drug Administration in the United States.

As sophisticated biological interface systems are approved by the FDA and become commercially available, these systems need to include numerous safety features required for medical devices. It may also be required that the systems have simplified configuration routines, such as patient training routines, which have minimal requirements and assure reliable functionality. Convenience and flexibility to the patient, their caregivers and family members, may also be necessary. There is therefore a need for an improved biological interface system which includes an automated patient training routine that can be utilized by a patient without need for another person at his or her site.

SUMMARY OF THE INVENTION

According to one exemplary aspect of the invention, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. A visual display is included to provide visual images to the patient. The system further comprises an integrated patient routine, such as an integrated software module of the system, that is performed to generate one or more system configuration parameters or values, these parameters used by the processing unit to produce the processed signals. The integrated patient routine provides a visual representation of a human figure to the patient on the visual display. The visual representation includes multiple human body movements provided for the patient to imagine similar movements. The system stores, such as in internal memory of one or more system components, a set of multicellular signals detected by the sensor simultaneous with the patient imagining the movements.

The representation of the human figure may be a series of photographs or a continuous video of an actor performing one or more motions. Alternatively the human figure may be a series of artistic sketches that are digitally scanned or captured, or a computer animated motion of a simulated human. In a preferred embodiment, multiple groups of series of motions, such as those representing left and right arm, elbow, wrist and/or finger motion, and left and right leg, hip, knee, ankle and/or toe motion, and an operator such as the patient or the patient's clinician can choose the group to be provided to the patient in the patient training routine. In a preferred embodiment, the body side chosen is the dominant side for the patient, such as the dominant side prior to an injury, and/or the body portion chosen corresponds to the location of the sensor, such as choosing left arm motions when a sensor has been placed in the left arm area of the patient's motor cortex. In another preferred embodiment, other features can be adjusted such as gender and age. In yet another preferred embodiment, multiple forms of feedback are provided to the patient, such as audio feedback including spoken words, and the language of the spoken words is adjustable by an operator of the system.

In an embodiment, the patient training routine can be performed without the need for an operator in addition to the patient. In another preferred embodiment, a operator at a remote location is utilized to complete the patient training routine. The patient training routine may be an embedded software routine located in a system at the patient site, or at a remote location. The patient training routine preferably comprises a set of steps, such as a set of steps that advance as triggered by one or more events, such as the successful completion of a task, or an input signal from the patient such as a monitored biologic signal or the activation of a patient switch such as a tongue switch. In another preferred embodiment, the series of steps self-adjusts or adapts based on one or more events such as a measure of patient performance. Each time the patient training routine is performed, a patient training event, the system configuration parameters generated may be used to build a transfer function applied to the multicellular signals to produce the processed signals.

According to another aspect of the invention, a system troubleshooting routine is integrated into the biological interface system of the present invention. The system troubleshooting routine can be performed when unsatisfactory system performance is detected or otherwise suspected, or may be performed as a diagnostic routine. The integrated system troubleshooting routine is performed to modify one or more system configuration parameters to improve system performance. The system troubleshooting routine includes similar additions and modifications to the patient training routine described hereabove, and similarly provides a visual representation of a human figure to the patient, and can be conducted with or without operators in addition to the patient, such as an operator at a location remote from the patient in communication with the biological interface system via the internet utilizing a remote access routine.

According to yet another aspect of the invention, a biological interface system is disclosed. The biological interface system collects multicellular signals emanating from one or more living cells of a patient and transmits processed signals to a controlled device. The system includes a sensor for detecting multicellular signals, the sensor comprising a plurality of electrodes. The electrodes are designed to detect the multicellular signals. A processing unit is designed to receive the multicellular signals from the sensor and process the multicellular signals to produce the processed signals transmitted to the controlled device. The system further comprises an integrated patient routine, such as an integrated software module of the system, that is performed to generate one or more system configuration parameters or values, these parameters used by the processing unit to produce the processed signals. The patient training routine includes a system configuration plan comprising a first configuration of steps to be performed. The patient training routine includes means of collecting and analyzing a first set of patient data. The first set of data is analyzed and produces one or more outputs of the analysis. The patient training routine further includes means of modifying the system configuration plan, such as to improve the patient training routine in subsequent steps. The configuration plan is modified when the one or more outputs of the analysis of the first set of patient data falls below a success threshold value.

In some exemplary embodiments, the first set of patient data is collected prior to the patient controlling the controlled device, or a controlled device surrogate, such as a surrogate to be used in subsequent steps of the patient training routine. In another exemplary embodiment, the first set of data does not include data of the patient controlling the controlled device or a controlled device surrogate. The first set of data preferably includes multicellular data, such as neural data including neural firing rates or information regarding neural firing rates. In an alternative or additional embodiment, the first set of data includes other patient physiologic data such as data collected with an additional sensor of the system. This additional physiologic data may include heart rate, blood pressure, respiration, blood glucose, and/or other physiologic information. In an embodiment, the first set of data is collected while the patient is provided a time varying stimulus, such as a representation of a human figure including multiple body movements, a different moving visual stimulus on a display screen, or a moving object such as a robotic arm or the patient's own limb being controlled, such as via FES or an exoskeleton, by a signal created by a system component.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings.

DESCRIPTION OF THE EMBODIMENTS

Figure 1:
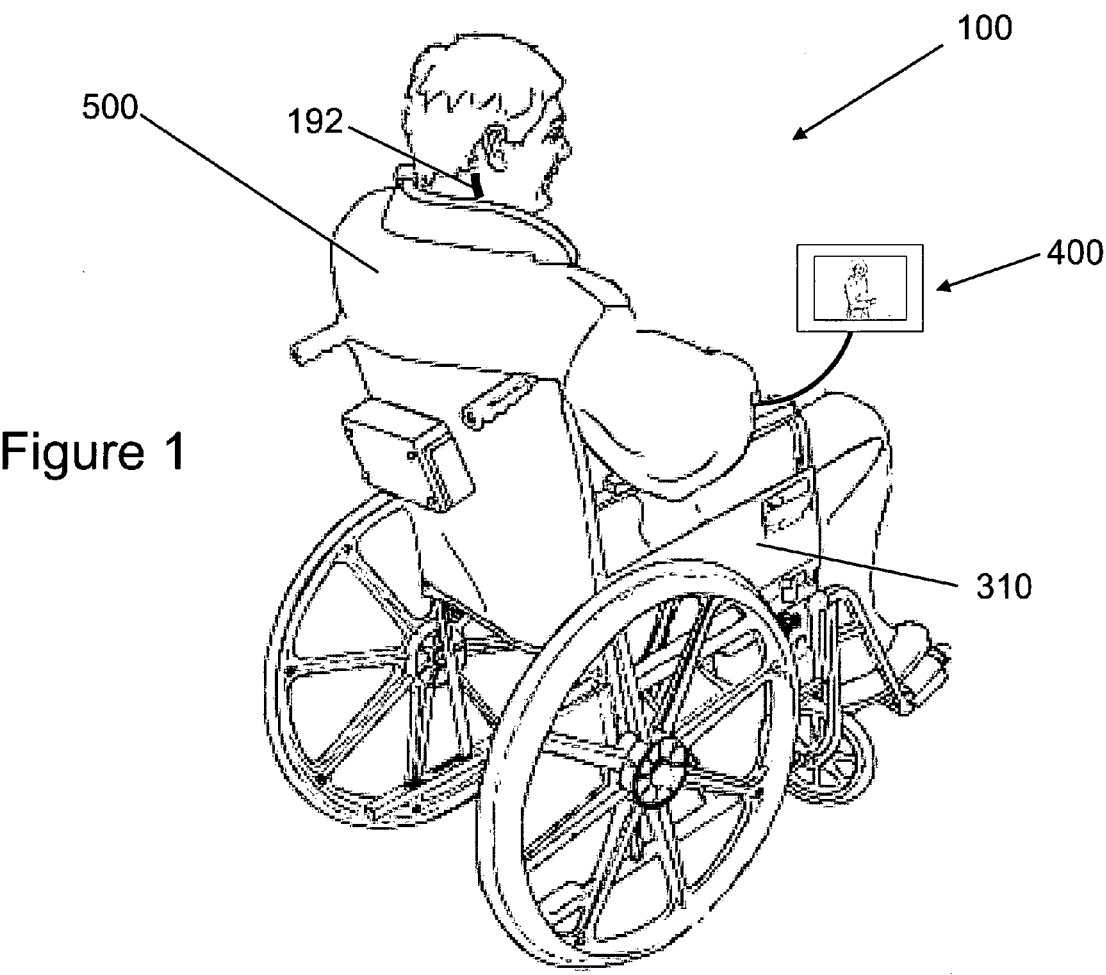
FIG. 1 illustrates an exemplary embodiment of a biological interface system consistent with the present invention wherein a wheelchair bound patient conducts a patient training routine without need for another operator.

To facilitate an understanding of the invention, a number of terms are defined immediately herebelow.

Definitions

As used herein, the term "biological interface system" refers to a neural interface system or any system that interfaces with living cells that produce electrical activity or cells that produce other types of detectable signals.

The term "cellular signals," as used herein, refers to signals or combination of signals that may emanate from any living cell, such as, for example, subcellular signals, intracellular signals, and extracellular signals. For example, "cellular signals" may include, but not be limited to: neural signals (e.g., neuron action potentials or spikes, local field potential (LFP) signals, electroencephalogram (EEG) signals, electrocorticogram signals (ECoG), and signals whose frequency range falls between single neuron spikes and EEG signals); cardiac signals (e.g., cardiac action potentials); electromyogram (EMG) signals; glial cell signals; stomach cell signals; kidney cell signals; liver cell signals; pancreas cell signals; osteocyte cell signals; sensory organ cell signals (e.g., signals emanating from the eye or inner ear); tumor cell signals; and tooth cell signals.

The term "multicellular signals," as used herein, refers to signals emanating from two or more cells, or multiple signals emanating from a single cell. The term "subcellular signals," as used herein, refers to, for example, a signal derived from a part of a cell, a signal derived from one particular physical location along or within a cell, a signal from a cell extension (e.g., dendrite, dendrite branch, dendrite tree, axon, axon tree, axon branch, pseudopod, or growth cone), and signals from organelles (e.g., golgi apparatus or endoplasmic reticulum). The term "intracellular signals," as used herein, refers to a signal that is generated within a cell or by the entire cell that is confined to the inside of the cell up to and including the membrane. The term "extracellular signals," as used herein, refers to signals generated by one or more cells that occur outside of the cell(s).

As used herein, the term "patient" refers to any animal, such as a mammal and preferably a human. Specific examples of a "patient" include, but are not limited to: individuals requiring medical assistance; healthy individuals; individuals with limited function; and individuals with lost motor or other function due to traumatic injury or neurological disease.

As used herein, the term "configuration" refers to any alteration, improvement, repair, calibration, or other system modifying event whether manual in nature or partially or fully automated. The term "configuration parameter," as used herein, refers to a variable, or a value of the variable, of a component, device, apparatus, and/or system. A configuration parameter has a value that can be: set or modified; used to perform a function; used in a mathematical or other algorithm; used as a threshold value to perform a comparison; and any combinations thereof. A configuration parameter's value determines the characteristics or behavior of something. System configuration parameters are variables of the system of the present invention, such as those used to by the processing unit to produce processed signals.

Other, numerous subsets of configuration parameters are applicable, these subsets including but not limited to: calibration parameters such as a calibration frequency parameter; controlled device parameters such as a time constant parameter; processing unit parameters such as a cell selection criteria parameter; patient parameters such as a patient physiologic parameter such as heart rate; multicellular signal sensor parameters; other sensor parameters; system environment parameters; mathematical algorithm parameters; a safety parameter; and other parameters. Certain parameters may be controlled by the patient's clinician, such as a password-controlled parameter securely controlled by an integral permission routine of the system. Certain parameters may represent a "threshold" such as a success threshold used in a comparison to determine if the outcome of an event was successful. In numerous steps of a system configuration or other function, a minimum performance or other measure may be maintained by comparing a detected signal, or the output of an analysis of one or more signals, to a success threshold.

As used herein, the term "discrete component" refers to a component of a system such as those defined by a housing or other enclosed or partially enclosed structure, or those defined as being detached or detachable from another discrete component. Each discrete component can transmit information to a separate component through the use of a physical cable, including one or more of electrically conductive wires or optical fibers, or transmission of information can be accomplished wirelessly. Wireless communication can be accomplished with a transceiver that may transmit and receive data such as through the use of "Bluetooth" technology or according to any other type of wireless communication means, method, protocol or standard, including, for example, code division multiple access (CDMA), wireless application protocol (WAP), Infrared or other optical telemetry, radio frequency or other electromagnetic telemetry, ultrasonic telemetry or other telemetric technologies.

As used herein, the term "routine" refers to an established function, operation, or procedure of a system, such as an embedded software module that is performed or is available to be performed by the system. Routines may be activated manually such as by an operator of a system, or occur automatically such as a routine whose initiation is triggered by another function, an elapsed time or time of day, or other trigger. The devices, apparatus, systems and methods of the present invention may include or otherwise have integrated into one or their components, numerous types and forms of routines. An "adaptive processing routine" is activated to determine and/or cause a routine or other function to be modified or otherwise adapt to maintain or improve performance. A competitive routine is activated to provide a competitive function for the patient of the present invention to compete with, such as a function which allows an operator of the system to compete with the patient in a patient training task; or an automated system function which controls a visual object which competes with a patient controlled object. A "configuration routine" is activated to configure one or more system configuration parameters of the system, such as a parameter that needs an initial value assigned or a parameter that needs an existing parameter modified. A "language selection routine" is activated to change a language displayed in text form on a display and/or in audible form from a speaker. A "patient training routine" is activated to train the patient in the use of the system and/or train the system in the specifics of the patient, such as the specifics of the patient's multicellular signals that can be generated by the patient and detected by the sensor. A "permission routine" is activated when a system configuration or other parameter is to be initially set or modified in a secured manner. The permission routine may use one or more of: a password; a restricted user logon function; a user ID; an electronic key; a electromechanical key; a mechanical key; a specific Internet IP address; and other means of confirming the identify of one or more operators prior to allowing a secure operation to occur. A "remote technician routine" is activated to allow an operator to access the system of the present invention, or an associated device, from a location remote from the patient, or a system component to be modified. A "system configuration routine" is activated to configure the system, or one or more components or associated devices of the system. In a system configuration routine, one or more system configuration parameters may be modified or initially set to a value. A "system reset routine" is activated to reset the entire system or a system function. Resetting the system is sometimes required with computers and computer based devices such as during a power failure or a system malfunction.

General Description of the Embodiments

Systems, methods, apparatus and devices consistent with the invention detect cellular signals generated within a patient's body and implement various signal processing techniques to generate processed signals for transmission to one or more devices to be controlled. The system includes a sensor, comprising a plurality of electrodes that detect multicellular signals from one or more living cells, such as from the central or peripheral nervous system of a patient. The system further includes a processing unit that receives and processes the multicellular signals and transmits a processed signal to a controlled device. The processing unit utilizes various electronic, mathematic, neural net and other signal processing techniques in producing the processed signal.

An integrated patient training routine is embedded in one or more components of the system. The patient training routine utilizes a visual display of the system to provide a visual representation of a human figure to the patient. This visual representation includes multiple human body movements that are used by the patient to imagine various movements. The system stores a set of multicellular signals while the patient imagines the movements, and uses the stored signals to generate one or more system configuration parameters, including parameter values such as initial values and modified values. These configuration parameters are used to produce a transfer function that is applied to subsequent multicellular signals to produce the processed signals used to control one or more controllable devices. The patient training routine may be a requirement of the system prior to allowing full control of the controlled device to the patient. The patient training routine may adapt over time, such as to improve system performance and/or reduce the patient requirements of the routine. The patient training routine may provide a system configuration plan, and the configuration plan may be adjusted based on the measurement of one or more parameters that are collected prior to requiring the patient to control a controlled device or a surrogate of a controlled device. The patient training routine may require no operator other than the patient, or may work with an operator at a remote location, such as a clinical site or a service group of the manufacturer of the biological interface system.

The visual representation of the human figure may be picture based, such as pictures from a video or digital camera of an actor providing the human movements, or may be a digital image or animation of one or more drawing or computer generated human figure graphics. The human figure may be adjustable, such as by the patient, these adjustments including whether the movements are accomplished by left or ride side body limbs, and which gender should be represented. Modifications such as these can be accomplished with the use of a patient input device, such as a neck switch or other input device. Additional feedback can be provided to the patient, simultaneously or at a different time, such as audio feedback provided through one or more speakers. This audio feedback may include combinations of tones or spoken language. The additional feedback is provided to improve the quality of the system configuration parameters generated, to generate additional system configuration parameters, and/or provide an additional function. Other forms of feedback can be additionally or alternatively provided to the patient, such as feedback selected from the group of: visual; tactile; auditory; olfactory; gustatory; electrical stimulation such as cortical stimulation; and combinations of the preceding. Additional visual feedback may include a second visual representation of a human figure, provided simultaneous with the first human figure or at different times.

DETAILED DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Referring now to FIG. 1, an exemplary embodiment of the present invention is illustrated wherein a patient conducts a patient training routine integral to a biological interface system wherein a visual representation of a human figure is provided to the patient. Biological interface system 100 includes this integral patient training routine, such as a software program or routine which is stored in volatile or non-volatile memory of one or more system components, including implanted components. In an alternative embodiment, one or more components of system 100 are at a site remote from the patient, such as a service bureau of the manufacturer, and the patient training routine software module is completely or partially stored in this remote site component. The visual representation of the patient training routine provides a series of movements for the patient to imagine, such as via a series of pictures or a video of an actor demonstrating the movements. During the imagined movements, a set of multicellular signals received by the processing unit from the sensor are stored in system memory. The patient training routine is used to generate one or more system configuration parameters, such as parameters that are used to generate a transfer function applied to multicellular signals to produce the processed signal. These system configuration parameters are preferably generated by performing an analysis of the stored multicellular signals that have been temporally correlated with the multiple human body movements provided by the patient training routine.

Patient 500 has been implanted with a sensor, not shown, such as one or more groups of electrodes placed in the motor cortex of a patient. These sensor components are attached with wires or wire bundles to a processing unit, or processing units, also not shown but at least one of which is fully implanted in the patient. The processing unit receives multicellular signals detected by the sensor electrodes and applies a transfer function to these signals to produce processed signals, which are control signals used to control one or more controllable devices. The implanted processing unit, or processing unit portion, communicates with a system component external to the patient via wireless communication means such as infrared or radiofrequency (RF) transmissions. Patient 500 is depicted in wheelchair 310, which is preferably a controlled device of biological interface system 100. Patient 500 has limited control of one or more legs, such as a paraplegic, and further may have limited use of one or more arms such as is often encountered in spinal cord injury and ALS patients.

Figure 1A:
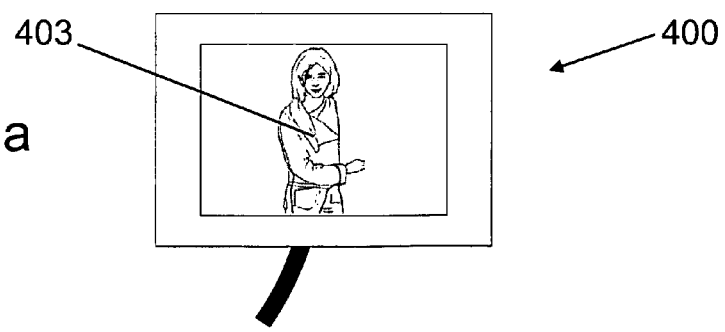
FIG. 1a illustrates a patient training visual display of the system of FIG. 1, consistent with the present invention.

Wheelchair 310 has mounted on an armrest selector module 400, which can be used by an operator of the system, such as the patient, to select one or more controlled devices to receive the processed signal. Selector module 400 preferably includes a touch screen display, this display also providing the visual representation of the human figure to the patient. Referring additionally to FIG. 1*a*, human FIG. 403 presents to patient 500 the multiple human body movements used by patient 500 to imagine the movements that correspond with the set of multicellular signals stored in a memory component of the system. The patient training routine is configured to allow the patient to perform the routine without the assistance of a second operator of the system. In an alternative embodiment, the patient routine utilizes a second operator, such as an operator at the patient site, or at a location remote from the patient communicating with system 100 via the Internet.

The patient training routine includes a series of steps to be completed, including one or more discrete segments of human body movements provided on selector module 400. The steps of the routine advance upon an event, such as the completion of a task as detected by the system or based on a patient or other operator input. In order for the system to determine a specific task has been successfully completed, an analysis of the performance may be compared to a threshold value, such as a threshold value that can be adjusted by an approved operator of the system such as the patient's clinician. In a preferred embodiment, when an unsuccessful task is determined, the specific step may be repeated, with or without modification of the step, a different step performed, or other modification. In another preferred embodiment, one or more sequences of steps advance based on a fixed time period expiring. If a step progresses due to a timeout, a modified sequence, such as a different next step may be implemented. Patient 500 is depicted with neck switch 192, such that specific motions of patient 500's head will activate one or more states of neck switch 192, these state changes provided via wireless communication means to one or more components of system 100. Additional or alternative patient input devices can be used, these devices selected from the group consisting of: chin joystick; eyebrow EMG switch such as an eyebrow EMG switch manufactured by Words+ Inc. of Lancaster, Calif.; EEG activated switch such as the switched manufactured by BrainFingers of Yellow Springs, Ohio, USA; eye tracker such as the device manufactured by LC Technologies of Fairfax, Va., USA; a head tracker such as the device manufactured Synapse Adaptive of San Rafael, Calif., USA; neck movement switch; shoulder movement switch; Sip n' Puff joystick controller such as the controller manufactured by QuadJoy of Sheboygan, Wis., USA; speech recognition switch; tongue switch such as a tongue palate switch; and combinations of the preceding. Other input devices, for the patient or a different operator, such as an operator at a location remote from the patient, may be included to provide input to the patient training program.

The patient training program may include one or more iterative loops of steps, such as: a repeating group of steps that are repeated for a fixed number of cycles or fixed period of time; a group of steps that are repeated until a performance level is achieved, such as a performance level which increases or decreases based on the performance level during a prior group of steps that were completed; and/or steps repeated based on an operator input parameter. These iterative loops of steps may include multiple segments of multiple human body movements, wherein one or more of these multiple segments may not be used in every patient training routine performed. Based on the number of iterative loops, operator input and/or patient 500 performance, the patient training routine performed may be shorter or longer than the performance of the patient training routine at a different time. In a preferred embodiment, the patient training routine is shorter in duration when performance is above a threshold value, and longer in duration when performance is below a threshold value.

The patient training routine may include two discrete parts. Multiple second parts may be integral to the patient training routine software module, wherein a specific second part is chosen based on the performance of patient 500 in the first part. Performance may include the number of cells providing signals to the set of multicellular signals received, the modulation rates or other modulation parameter of one or more of these cellular signals, and/or other measurable parameter. The second part chosen may be determined in whole or in part, with a patient input signal, such as from one or more of the devices listed hereabove. In another preferred embodiment, the patient training routine adapts, such as an automatic adaptation that occurs within a single patient training event or between a first patient training event and a second patient training event. The adaptation may include a change to one or more parameters of the patient training routine, such as the set of multicellular signals processed to modify a system configuration parameter, a parameter determining which human body movements that are provided to the patient, a configuration of additional feedback provided to the patient, and/or other parameter.

The system configuration parameter or parameters, including the initial and modified values of these parameters, which are generated by the patient training routine, can be used by the system to perform one or more functions, preferably used in a transfer function applied to the multicellular signals to produce the processed signals of system 100. In a preferred embodiment, the parameters are selected from the group consisting of: selection of cells for processing; criteria for the selection of cells to be processed; a computational or other signal processing parameter; a signal transfer function parameter such as a transfer function coefficient for an algorithm, methodology or mathematical equation; a calibration routine parameter such as calibration frequency; a controlled device parameter such as a controlled device boundary limit such as a maximum velocity or maximum position; and combinations of the preceding. In another preferred embodiment, the parameters are selected from the group consisting of: acceptable frequency range of cellular activity; cellular signal amplitude threshold value; selection of electrodes to include; selection of cellular signals to include; type of frequency analysis such as power spectral density; instruction information to patient such as imagined movement type or other imagined movement instruction; type, mode or configuration of feedback during provision of processed signal to patient; controlled device parameter such as controlled device mode; alarm or alert threshold value; success threshold value; and combinations thereof.

When the patient training routine of system 100 has performed one or more analyses to generate a system configuration parameter value or value modification, a permission routine of the system may be invoked prior to implementation or full implementation of the change. The permission routine may require confirmation of the new configuration parameter value by an operator, further including: a specific user ID or password; a specific IP address for a remote operator; a mechanical, electronic, or electromechanical key; and/or other confirming operator requirement. In another preferred embodiment, the patient confirms the new configuration parameter value, such as via a chin joystick or other patient input device as has been listed hereabove.

In an alternative embodiment, the biological interface system of the present invention alternatively or additionally includes a system troubleshooting routine. The biological interface system collects multicellular signals emanating from one or more living cells of a patient and transmits processed signals to one or more controllable devices. The system includes a sensor that detects the multicellular signals and comprises a plurality of electrodes that detect the multicellular signals. The system also includes a processing unit that receives the multicellular signals from the sensor, processes the multicellular signals to produce processed signals, and transmits the processed signals to at least one controlled device. A system troubleshooting routine is integrated into one or more components of the biological interface system, such as a software module integrated into volatile or nonvolatile memory used by a microprocessor or other microcontroller based system. The software module may be integral to a component internal to the patient, or external to the patient such as in a component proximate the patient or at a site remote from the patient. An operator, such as the patient or a non-patient operator at a location remote from the patient and accessing the system via a computer network, performs the system troubleshooting routine to improve system performance by modifying one or more system configuration parameters or parameter values. The processing unit uses these parameters to produce the processed signals transmitted to the controlled device. Prior to modifying or setting a configuration parameter, a permission routine may be invoked as has been described in detail hereabove in reference to changing a parameter of the patient training routine. The integrated system troubleshooting routine provides a visual representation of a human figure to the patient. The visual representation preferably includes multiple human body movements, and can comprise visual images of a human actor, or can be an animated image such as a computer animated human figure. The multiple human body movements may be provided as a time varying stimulus and used by the patient to imagine one or more movements or other imagined states that are stored in system memory, and preferably temporally correlated to the visual representation of the human figure.

The system troubleshooting routine of the present invention includes one or more similar functions of the patient training routine described in reference to FIG. 1 hereabove. For example, the system troubleshooting routine may incorporate audio feedback provided to the patient utilizing a speaker. The audio feedback may include spoken words, such as words provided in a language adjustable by the patient or other operator utilizing one or more input devices. Additional feedback can be provided to the patient, such as a second visual representation of a human figure, provided simultaneous with the first human figure or at different times. Other feedback as described in reference to the patient training routine can be included such as feedback selected from the group consisting of: visual; tactile; auditory; olfactory; taste; electrical stimulation; and combinations thereof. The performance of the system troubleshooting routine preferably stores one or more sets of data.

The system troubleshooting routine preferably includes a set of steps, again similar to the patient training routine, the set of steps including multiple discrete segments of feedback provided to the patient, such as visual feedback including the visual representation of a human figure. The steps can progress as described in reference to the patient training routine steps, such as via a patient input device, a completed or successfully completed patient task, or after an expired duration of time. The steps may similarly include one or more iterative loops, and the system trouble shooting routine includes a first part that can progress to one or more second parts, such as multiple second parts selected via a performance value from the first part. In a preferred embodiment, the system troubleshooting routine similarly adapts, such as an adaptation within a single system troubleshooting routine event, or from a first patient training routine event to a second patient training routine event.

Figure 2:
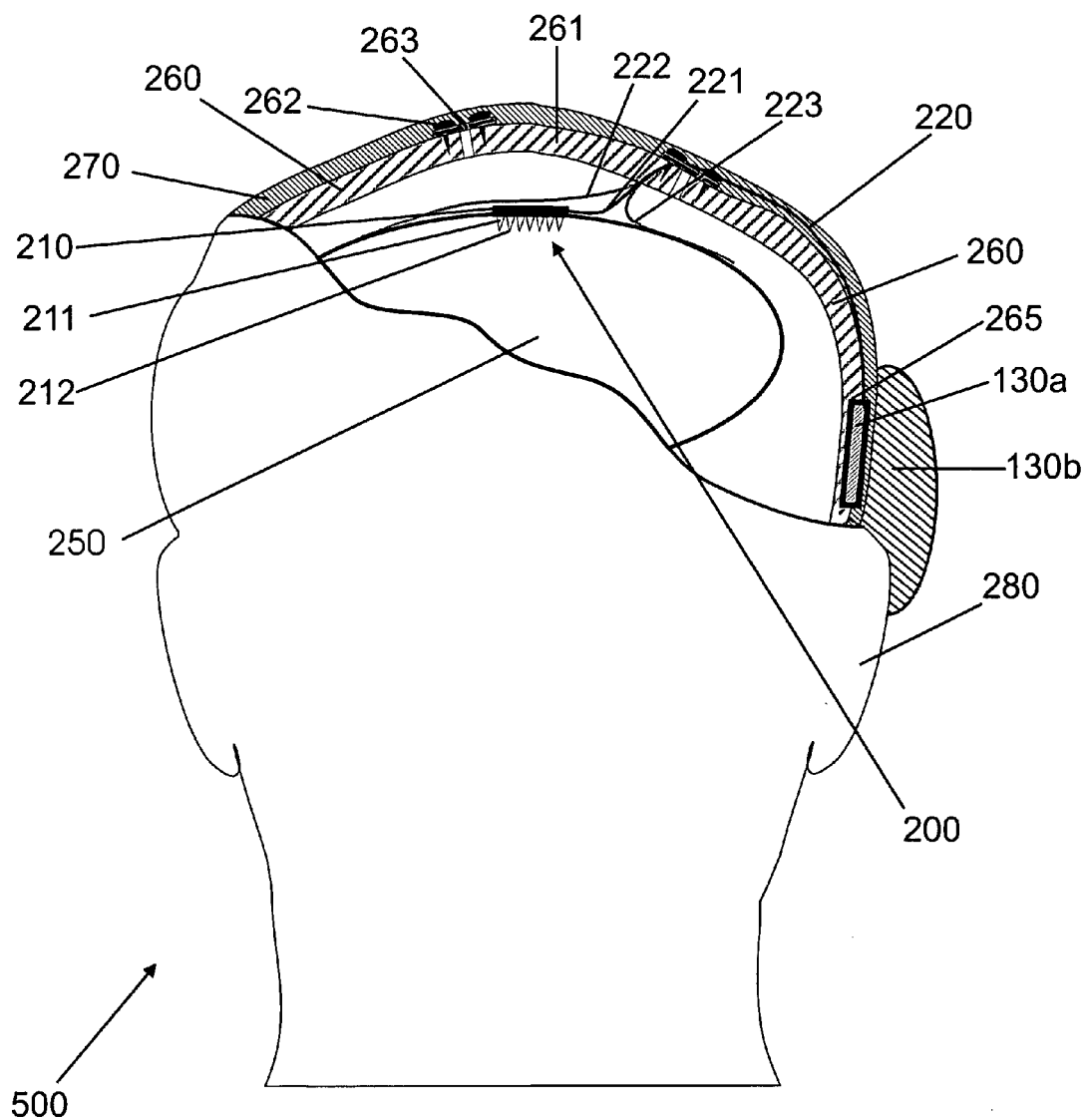
FIG. 2 illustrates an exemplary embodiment of a portion of the biological interface system consistent with the present invention wherein sensor electrodes are implanted in the brain of a patient and a portion of a processing unit is implanted on the skull of the patient.

Referring now to FIG. 2, a brain implant apparatus consistent with an embodiment of the present invention is illustrated. As shown in FIG. 2, the system includes an array of electrodes assembly, sensor 200, which has been inserted into a brain 250 of patient 500, through a previously created opening in scalp 270 and skull 260 in a surgical procedure known as a craniotomy. Sensor 200 includes a plurality of longitudinal projections 211 extending from a base, array substrate 210. Projections 211 may be rigid, semi-flexible or flexible, the flexibility such that each projection 211 can still penetrate into neural tissue, potentially with an assisting device or with projections that only temporarily exist in a rigid condition. Sensor 200 has been inserted into brain 250, preferably using a rapid insertion tool, such that the projections 211 pierce into brain 250 and sensor substrate 210 remains in close proximity to or in light contact with the surface of brain 250. At the end of each projection 211 is an electrode, electrode 212. In alternative embodiments, electrodes can be located at a location other than the tip of projections 211 or multiple electrodes may be included along the length of one or more of the projections 211. One or more projections 211 may be void of any electrode, such projections potentially including anchoring means such as bulbous tips or barbs, not shown.

Electrodes 212 are configured to detect electrical brain signals or impulses, such as individual neuron spikes or signals that represent clusters of neurons such as local field potential (LFP) and electroencephalogram (EEG) signals. Each electrode 212 may be used to individually detect the firing of multiple neurons, separated by neuron spike discrimination techniques. Other applicable signals include electrocorticogram (ECOG) signals and other signals, such as signals between single neuron spikes and EEG signals. Sensor 200 may be placed in any location of a patient's brain allowing for electrodes 212 to detect these brain signals or impulses. In a preferred embodiment, electrodes 212 can be inserted into a part of brain 250 such as the cerebral cortex. Alternative forms of penetrating electrodes, such as wire or wire bundle electrodes, can make up or be a component of the sensor of the present invention. In addition to or alternative from neural signals, the system of the present invention may utilize other types of cellular signals to produce processed signals to control a device. The various forms of penetrating electrodes described above can be placed into tissue within or outside of the patient's cranium, such tissue including but not limited to: nerve tissue such as peripheral nerve tissue or nerves of the spine; organ tissue such as heart, pancreas, liver or kidney tissue; tumor tissue such as brain tumor or breast tumor tissue; other tissue and combinations of the preceding, Alternatively or additionally, the sensor of the present invention may employ non-penetrating electrode configurations, not shown, such as subdural grids placed inside the cranium such as to record LFP signals. In addition to subdural grids, the sensor may comprise other forms of non-penetrating electrodes such as flat electrodes, coil electrodes, cuff electrodes and skin electrodes such as scalp electrodes. These non-penetrating electrode configurations are placed in, on, near or otherwise in proximity to the cells whose signals are to be detected, such as neural or other cellular signals. In another alternative embodiment, the sensor of the present invention includes detectors other than electrodes, such as photodetectors that detect cellular signals represented by a light emission. The light emission can be caused by a photodiode, integrated into the sensor or other implanted or non-implanted system component, shining one or more wavelengths of light on the appropriate cells. In addition to the numerous types of cells described above, one or more of the various configurations of the sensor of the present invention may utilize any living cell of the body that emanates cellular signals. In a preferred embodiment, the cellular signals are under voluntary control of the patient.

Although FIG. 2 depicts sensor 200 as a single discrete component, in alternative embodiments the sensor comprises multiple discrete components, including one or more types of electrodes or other cellular signal detecting elements, each configured and placed to detect similar or dissimilar types of cellular signals. Multiple sensor discrete components can be implanted entirely within: the skull, an extracranial location such as a peripheral nerve, or external to the body; or the components can be placed in any combination of these locations.

Sensor 200 serves as the multicellular signal sensor of the biological interface system of the present invention. While FIG. 2 shows sensor 200 as eight projections 211 with eight electrodes 212, sensor 200 may include one or more projections with and without electrodes, both the projections and electrodes having a variety of sizes, lengths, shapes, surface areas, forms, and arrangements. Moreover, sensor 200 may be a linear array (e.g., a row of electrodes) or a two-dimensional array (e.g., a matrix of rows and columns of electrodes such as a ten by ten array), or wire or wire bundle electrodes, all well known to those of skill in the art. An individual wire lead may include a plurality of electrodes along its length. Projections and electrodes may have the same materials of construction and geometry, or there may be varied materials and/or geometries used in one or more electrodes. Each projection 211 and electrode 212 of FIG. 2 extends into brain 250 to detect one or more cellular signals such as those generated form the neurons located in proximity to each electrode 212's placement within the brain. Neurons may generate such signals when, for example, the brain instructs a particular limb to move in a particular way and/or the brain is planning that movement. In a preferred embodiment, the electrodes reside within the arm, hand, leg or foot portion of the motor cortex of the brain. The processing unit of the present invention may assign one or more specific cellular signals to a specific use, such as a specific use correlated to a patient imagined event. In a preferred embodiment, the one or more cellular signals assigned to a specific use are under voluntary control of the patient.

Referring back to FIG. 2, the processing unit of the present invention includes processing unit first portion 130a, placed under the scalp at a location near patient 500's ear 280. Processing unit first portion 130a receives cellular signals from sensor 200 via wire bundle 220, a multi-conductor cable. In a preferred embodiment, wire bundle 220 includes a conductor for each electrode 212. Processed signals are produced by processing unit first portion 130a and other processing unit discrete components, such as processing unit second portion 130b removably placed on the external skin surface of patient 500 near ear 280. Processing unit second portion 130b remains in relative close proximity to implanted component processing unit first portion 130a through one or more fixation means such as cooperative magnetic means in both components, or body attachment means such as where the processing unit second portion 130b is attached to eye glasses, an ear wrapping arm, a hat, mechanical straps or an adhesive pad. Processing unit first portion 130a and processing unit second portion 130b work in combination to receive multicellular signal data and create a time code of brain activity.

In the preferred embodiment depicted in FIG. 2, bone flap 261, the original bone portion removed in the craniotomy, has been used to close the hole made in the skull 260 during the craniotomy, obviating the need for a prosthetic closure implant. Bone flap 261 is attached to skull 260 with one or more straps, bands 263, which are preferably titanium or stainless steel. Band 263 is secured to bone flap 261 and skull 260 with bone screws 262. Wire bundle 220 passes between bone flap 261 and the hole cut into skull 260. During the surgical procedure, bone recess 265 was made in skull 260 such that processing unit first portion 130a could be placed in the indentation, allowing scalp 270 to lie relatively flat and free of tension in the area proximal to processing unit first portion 130a. A long incision in scalp 270 between the craniotomy site and the recess 265 can be made to place processing unit first portion 130a in recess 265. Alternatively, an incision can be made to perform the craniotomy, and a separate incision made to form recess 265, after which the processing unit first portion 130a and wire bundle 220 can be tunneled under scalp 270 to the desired location. Processing unit first portion 130a is attached to skull 260 with one or more bone screws or a biocompatible adhesive, not shown.

In an alternative embodiment, processing unit first portion 130a may be placed entirely within skull 260 or be geometrically configured and surgically placed to fill the craniotomy hole instead of bone flap 261. Processing unit first portion 130a can be placed in close proximity to sensor 200, or a distance of 5-20 cm can separate the two components. Processing unit first portion 130a includes a biocompatible housing which creates a fluid seal around wire bundle 220 and numerous internal components of processing unit first portion 130a, internal components not shown. Processing unit first portion 130a internal components provide the following functions: signal processing of the cellular signals received from sensor 200 such as buffering, amplification, digital conversion and multiplexing, wireless transmission of cellular signals, a partially processed, or derivative form of the cellular signals, or other data; inductive power receiving and conversion; and other functions well known to implanted electronic assemblies such as implanted pacemakers, defibrillators and pumps.

Processing unit second portion 130b, removably placed at a location proximate to implanted processing unit first portion 130a but external to patient 500, receives data from processing unit first portion 130a via wireless communication through the skin, such as infrared or radiofrequency wireless data transfer means. Processing unit second portion 130b, includes, in addition to wireless data receiving means, wireless power transfer means such as an RF coil which inductively couples to an implanted coil, signal processing circuitry, an embedded power supply such as a battery, and data transfer means. The data transfer means of processing unit second portion 130b may be wired or wireless, and transfer data to one or more of: implanted processing unit first portion 130a; a different implanted device; and an external device such as an additional component of the processing unit of the present invention, a controlled device of the present invention or a computer device such as a configuration computer with Internet access, all not shown.

Referring back to FIG. 2, electrodes 212 transfer the detected cellular signals to processing unit first portion 130a via array wires 221 and wire bundle 220. Wire bundle 220 includes multiple conductive elements, and array wires 221, which preferably include a conductor for each electrode of sensor 200. Also included in wire bundle 220 are two conductors, first reference wire 222 and second reference wire 223 each of which is placed in an area in relative proximity to sensor 200 such as on the surface of brain 250 near the insertion location. First reference wire 222 and second reference wire 223 may be redundant, and provide reference signals used by one or more signal processing elements of the processing unit of the present invention to process the cellular signal data detected by one or more electrodes. In an alternative embodiment, not shown, sensor 200 comprises multiple discrete components and multiple bundles of wires connect to one or more discrete components of the processing unit, such as processing unit first portion 130*a*. In another alternative embodiment, not shown, cellular signals detected by sensor 200 are transmitted to processing unit 130*a* via wireless technologies, such as infrared communication incorporated into an electronic module of sensor 200, such transmissions penetrating the skull of the patient, and obviating the need for wire bundle 220, array wires 221 and any physical conduit passing through skull 260 after the surgical implantation procedure is completed.

Processing unit first portion 130*a* and processing unit second portion 130*b* independently or in combination preprocess the received cellular signals (e.g., impedance matching, noise filtering, or amplifying), digitize them, and further process the cellular signals to extract neural data that processing unit second portion 130*b* may then transmit to an external device (not shown), such as an additional processing unit component and/or any device to be controlled by the processed multicellular signals. For example, the external device may decode the received neural data into control signals for controlling a prosthetic limb or limb assist device or for controlling a computer cursor. In an alternative embodiment, the external device may analyze the neural data for a variety of other purposes. In another alternative embodiment, the device receiving transmissions from processing unit second portion 130*b* is an implanted device. Processing unit first portion 130*a* and processing unit second portion 130*b* independently or in combination include signal processing circuitry to perform multiple signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controlled device. Processing unit first portion 130*a* and processing unit second portion 130*b* may include one or more components to assist in processing the multicellular signals or to perform additional functions. These components include but are not limited to: a temperature sensor; a pressure sensor; a strain gauge; an accelerometer; a volume sensor; an electrode; an array of electrodes; an audio transducer; a mechanical vibrator; a drug delivery device; a magnetic field generator; a photo detector element; a camera or other visualization apparatus; a wireless communication element; a light producing element; an electrical stimulator; a physiologic sensor; a heating element and a cooling element.

Processing unit first portion 130*a* transmits raw or processed cellular signal data to processing unit second portion 130*b* through integrated wireless communication means, such as the infrared communication means of FIG. 2, or alternative means including but not limited to radiofrequency communications, other optical communications, inductive communications, ultrasound communications and microwave communications. In a preferred, alternate embodiment, processing unit first portion 130*a* includes both infrared communication means for short-range high baud rate communication, and radiofrequency communication means for longer range, lower baud rate communication. This wireless transfer allows sensor 200 and processing unit first portion 130*a* to be completely implanted under the skin of the patient, avoiding the need for implanted devices that require protrusion of a portion of the device or wired connections through the skin surface. In an alternative embodiment, a through the skin pedestal connector is utilized between either the implanted sensor 200 or processing unit first portion 130*a* and an external component. Processing unit first portion 130*a* includes a coil, not shown, which receives power through inductive coupling, on a continual or intermittent basis from an external power transmitting device such as processing unit second portion 130*b*. The inductive coupling power transfer configuration obviates the need for any permanent power supply, such as a battery, integral to processing unit first portion 130*a*.

In addition to or in place of power transmission, the integrated coil of processing unit first portion 130*a* and its associated circuitry may receive data from an external coil whose signal is modulated in correlation to a specific data signal. The power and data can be delivered to processing unit first portion 130*a* simultaneously such as through simple modulation schemes in the power transfer that are decoded into data for processing unit first portion 130*a* to use, store or facilitate another function. A second data transfer means, in addition to a wireless means such as an infrared LED, can be accomplished by modulating a signal in the coil of processing unit first portion 130*a* that data is transmitted from the implant to an external device including a coil and decoding elements. In a preferred embodiment, the processing unit first portion 130*a* included an embedded ID, which can be wirelessly transmitted to the processing unit second portion 130*b* or a separate discrete component via the various wireless transmission means described above. In another preferred embodiment, processing unit second portion 130*b* includes means of confirming proper ID from processing unit first portion 130*a* and processing unit second portion 130*b* also included an embedded ID.

Processing unit first portion 130*a* and processing unit second portion 130*b* may independently or in combination also conduct adaptive processing of the received cellular signals by changing one or more parameters of the system to achieve acceptable or improved performance. Examples of adaptive processing include, but are not limited to, changing a system configuration parameter during a system configuration, changing a method of encoding neural or other cellular signal data, changing the type, subset, or amount of cellular signal data that is processed, or changing a method of decoding neural or other cellular signal data. Changing an encoding method may include changing neuron spike sorting methodology, calculations, thresholds, or pattern recognition methodologies. Changing a decoding methodology may include changing variables, coefficients, algorithms, and/or filter selections. Other examples of adaptive processing may include changing over time the type or combination of types of signals processed, such as EEG, ECoG, LFP, neural spikes, or other cellular signal types.

Processing unit first portion 130*a* and processing unit second portion 130*b* may independently or in combination also transmit electrical signals to one or more electrodes 212 such as to stimulate, polarize, hyperpolarize or otherwise cause an effect on one or more cells of neighboring tissue. Specific electrodes may record cellular signals only, or deliver energy only, and specific electrodes may provide both functions. In an alternative embodiment, a separate device, not shown but preferably an implanted device with the ability to independently or in combination provide an electrical signal to multiple electrodes, delivers stimulating energy to one or more electrodes 212 or different electrodes, also not shown. Stimulating electrodes in various locations can transmit signals to the central nervous system, peripheral nervous system, other body systems, body organs, muscles and other tissue or cells. The transmission of these signals is used to perform one or more functions including but not limited to: pain therapy; muscle stimulation; seizure disruption; stroke rehabilitation; coma recovery; and patient feedback.

In an alternative embodiment, not shown, processing unit first portion 130a, and potentially additional signal processing functions are integrated into sensor 200, such as through the use of a bonded electronic microchip. In another alternative embodiment, processing unit first portion 130a may also receive non-neural cellular signals and/or other biologic signals, such as from an implanted sensor. These signals may be in addition to received neural multicellular signals, and they may include but are not limited to: EKG signals, respiration signals, blood pressure signals, electromyographic activity signals and glucose level signals. Such biological signals may be used to change the state of the biological interface system of the present invention, or one of its discrete components. Such state changes include but are not limited to: turn system or component on or off; to begin a configuration routine; to initiate or conclude a step of a configuration or other routine; and to start or stop another system function. In another alternative embodiment, processing unit first portion 130a and processing unit second portion 130b independently or in combination produce one or more additional processed signals, to additionally control the controlled device of the present invention or to control one or more additional controlled devices.

In an alternative, preferred configuration of implanted components, not shown, a discrete component such as a sensor of the present invention is implanted within the cranium of the patient, such as sensor 200 of FIG. 2, a processing unit or a portion of a processing unit of the present invention is implanted in the torso of the patient, and one or more discrete components are external to the body of the patient. The processing unit may receive multicellular signals from the sensor via wired, including conductive wires and optic fibers, or wireless communication. The sensor 200 preferably includes signal processing means including signal processing up to and including digitizing the multicellular signals. In another alternative embodiment, preferably an acute (less than 24 hours) or sub-chronic (less than 30 days) application, a through the skin, or transcutaneous device is used to transmit or enable the transmission of the multicellular signals, and/or a derivative or pre-processed form of the multicellular signals.

Figure 3:
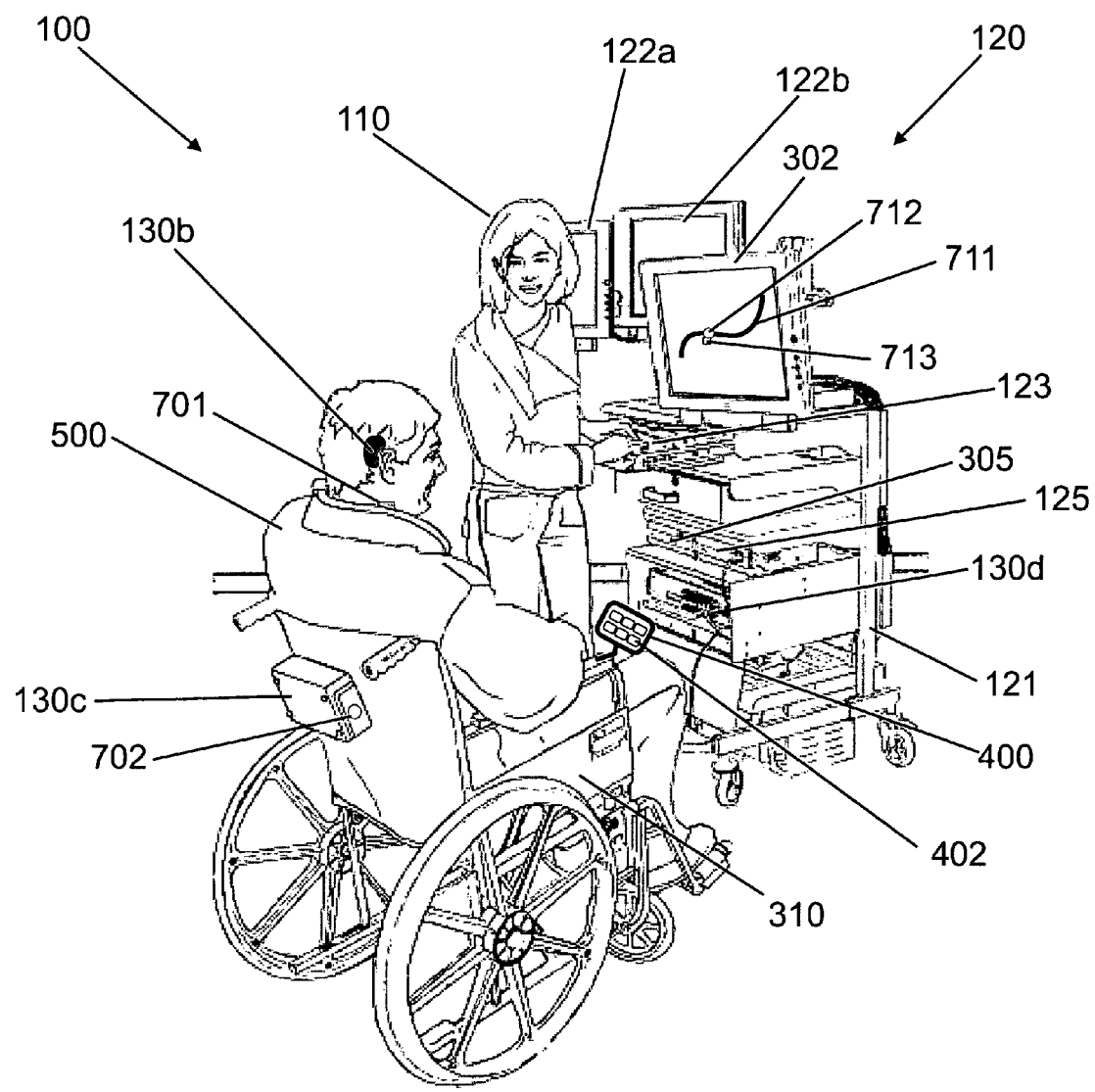
FIG. 3 illustrates another exemplary embodiment of a biological interface system consistent with the present invention wherein an operator configures the system at the patient site.

Referring now to FIG. 3, a biological interface system 100 is shown comprising implanted components, not shown, and components external to the body of a patient 500. A sensor for detecting multicellular signals, not shown and preferably a two dimensional array of multiple protruding electrodes, has been implanted in the brain of patient 500, in an area such as the motor cortex. In a preferred embodiment, the sensor is placed in an area to record multicellular signals that are under voluntary control of the patient. Alternatively or additionally to the two dimensional array, the sensor may include one or more wires or wire bundles which include a plurality of electrodes. Patient 500 of FIG. 3 is shown as a human being, but other mammals and life forms that produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device. Numerous types of patients, including healthy individuals, are applicable to the system of the present invention. The patient of the present invention may be a quadriplegic, a paraplegic, an amputee, a spinal cord injury victim or an otherwise physically impaired person. Alternatively or in addition, Patient 500 may have been diagnosed with one or more of: obesity, an eating disorder, a neurological disorder, a psychiatric disorder, a cardiovascular disorder, an endocrine disorder, sexual dysfunction, incontinence, a hearing disorder, a visual disorder, sleeping disorder, a movement disorder, a speech disorder, physical injury, migraine headaches or chronic pain. System 100 can be used to treat one or more medical conditions of patient 500, or to restore, partially restore, replace or partially replace a lost function of patient 500.

Alternatively, system 100 can be utilized by patient 500 to enhance performance, such as if patient 500 did not have a disease or condition from which a therapy or restorative device could provide benefit, but did have an occupation wherein thought control of a device provided an otherwise unachieved advancement in healthcare, crisis management and national defense. Thought control of a device can be advantageous in numerous healthy individuals including but not limited to: a surgeon, such as an individual surgeon using thought control to maneuver three or more robotic arms in a complex laparoscopic procedure or a surgeon controlling various instruments at a location remote from the instruments and the surgical procedure; a crisis control expert, such as a person who in attempting to minimize death and injury uses thought control to communicate different pieces of information and/or control multiple pieces of equipment, such as urban search and rescue equipment, simultaneously during an event such as an earthquake or other disaster, both natural disasters and those caused by man; a member of a bomb squad, such as an expert who uses thoughts to control multiple robots and/or robotic arms to remotely diffuse a bomb; and military personnel who use thought control to communicate with personnel and control multiple pieces of defense equipment, such as artillery, aircraft, watercraft, land vehicles and reconnaissance robots. It should be noted that the above advantages of system 100 to a healthy individual are also advantages achieved in a patient such as a quadriplegic or paraplegic. In other words, a quadriplegic could provide significant benefit to society, such as in controlling multiple bomb diffusing robots, in addition to his or her ambulation and other quality of life devices. Patients undergoing implantation and use of the system 100 of the present invention may provide numerous occupational and other functions not available to individuals that do not have the biological interface system of the present invention.

The sensor electrodes of system 100 can be used to detect various multicellular signals as has been described in detail in reference to FIG. 2 hereabove. The sensor is connected via a multi-conductor cable, not shown but also implanted in patient 500, to an implanted portion of the processing unit which includes some signal processing elements as well as wireless communication means as has been described in detail in reference to FIG. 2. The implanted multi-conductor cable preferably includes a separate conductor for each electrode, as well as additional conductors to serve other purposes, such as providing reference signals and ground. A second portion of the processing unit, processing unit second portion 130b receives the wireless communications from the implanted portion. Processing unit second portion 130*b* is removably located just above the ear of patient 500, such as to be aligned with an infrared data transmission element of the implanted device. Multicellular signals or derivatives of the multicellular signals are transmitted from the implanted processing unit component to processing unit second portion 130*b* for further processing. The processing unit components of system 100 perform various signal processing functions as have been described in detail in reference to FIG. 2. The processing unit may process signals that are mathematically combined, such as the combining of neuron spikes that are first separated using spike discrimination methods, these methods known to those of skill in the art. In alternative embodiments, the processing unit may comprise multiple components or a single component; each of the processing unit components can be fully implanted in patient 500, be external to the body, or be implanted with a portion of the component exiting through the skin.

In FIG. 3, a first controlled device is a computer, CPU 305 that is attached to monitor 302 and integrated into configuration cart 121. Through the use of system 100, patient 500 can control one or more computer functions including but not limited to: an on/off function, a reset function, a language function, a modem function, a printer function, an Internet function, a cursor, a keyboard, a joystick, a trackball or other input device. Each function may be controlled individually or in combination. System 100 includes a second controlled device, wheelchair 310. Numerous other controlled devices can be included in the systems of this application, individually or in combination, including but not limited to: a computer; a computer display; a mouse; a cursor; a joystick; a personal data assistant; a robot or robotic component; a computer controlled device; a teleoperated device; a communication device or system; a vehicle such as a wheelchair; an adjustable bed; an adjustable chair; a remote controlled device; a Functional Electrical Stimulator device or system; a muscle stimulator; an exoskeletal robot brace; an artificial or prosthetic limb; a vision enhancing device; a vision restoring device; a hearing enhancing device; a hearing restoring device; a movement assist device; medical therapeutic equipment such as a drug delivery apparatus; medical diagnostic equipment such as epilepsy monitoring apparatus; other medical equipment such as a bladder control device, a bowel control device and a human enhancement device; closed loop medical equipment and other controllable devices applicable to patients with some form of paralysis or diminished function as well as any device that may be utilized under direct brain or thought control in either a healthy or unhealthy patient.

Processing unit second portion 130*b* includes a unique electronic ID, such as a unique serial number or any alphanumeric or other retrievable, identifiable code associated uniquely with the system 100 of patient 500. The unique electronic identifier may take many different forms in processing unit second portion 130*b*, such as a piece of electronic data stored in a memory module; a semiconductor element or chip that can be read electronically via serial, parallel or telemetric communication; pins or other conductive parts that can be shorted or otherwise connected to each other or to a controlled impedance, voltage or ground, to create a unique code; pins or other parts that can be masked to create a binary or serial code; combinations of different impedances used to create a serial code that can be read or measured from contacts, features that can be optically scanned and read by patterns and/or colors; mechanical patterns that can be read by mechanical or electrical detection means or by mechanical fit, a radio frequency ID or other frequency spectral codes sensed by radiofrequency or electromagnetic fields, pads and/or other marking features that may be masked to be included or excluded to represent a serial code, or any other digital or analog code that can be retrieved from the discrete component.

Alternatively or in addition to embedding the unique electronic ID in processing unit second portion 130*b*, the unique electronic ID can be embedded in one or more implanted discrete components. Under certain circumstances, processing unit second portion 130*b* or another external or implanted component may need to be replaced, temporarily or permanently. Under these circumstances, a system compatibility check between the new component and the remaining system components can be confirmed at the time of the repair or replacement surgery through the use of the embedded unique electronic ID. The unique electronic ID can be embedded in one or more of the discrete components at the time of manufacture, or at a later date such as at the time of any clinical procedure involving the system, such as a surgery to implant the sensor electrodes into the brain of patient 500. Alternatively, the unique electronic ID may be embedded in one or more of the discrete components at an even later date such as during a system configuration routine such as a calibration routine.

Referring again to FIG. 3, processing unit second portion 130*b* communicates with one or more discrete components of system 100 via wireless communication means. Processing unit second portion 130*b* communicates with selector module 400, a component utilized to select the specific device or devices to be controlled by the processed signals of system 100. Selector module 400 includes a touch screen set of buttons, input element 402, used to perform the selection process. Processing unit second portion 130*b* also communicates with controlled device CPU 305, such as to control a cursor, joystick, keyboard or other function of CPU 305. Processing unit second portion 130*b* further communicates with processing unit third portion 130*c*. Processing unit third portion 130*c* provides additional signal processing functions, as have been described above, to control wheelchair 310. An additional processing unit discrete component, processing unit fourth portion 130*d*, is included to perform additional processing of the multicellular signals and/or derivatives of these processed signals and/or processing of additional information, such collective processing used to control one or more additional controlled devices of the present invention, not shown. System 100 of FIG. 3 utilizes selector module 400 to select one or more of CPU 305, wheelchair 310 or another controlled device to be controlled by the processed signals produced by the processing unit of the present invention. In system 100 of FIG. 3, one set of processed signals emanate from one portion of the processing unit, processing unit second portion 130*b*, and a different set of processed signals emanate from a different portion of the processing unit, processing unit third portion 130*c*.

The various components of system 100 communicate with wireless transmission means, however it should be appreciated that physical cables can be used to transfer data alternatively or in addition to wireless means. These physical cables may include electrical wires, optical fibers, sound wave guide conduits, and other physical means of transmitting data and/or power and any combination of those means.

Referring back to FIG. 3, a qualified individual, operator 110 in cooperation with patient 500, is performing a patient training routine, one of numerous configuration programs or routines of the system. In an alternative embodiment, patient 500 is the operator of the patient training routine or other configuration routine. The patient training routine is shown being performed with controlled device 305. Displayed on monitor 302 is planned trajectory 711, system controlled target 712 and patient controlled object 713. In the performance of the patient training routine, multiple time varying stimulus, such as a moving system controlled target 712 are provided to the patient such that the patient can imagine moving that target, and a set of multicellular signal data can be collected by the processing unit to produce one or more algorithms to produce the processed signals of the present invention. In a preferred embodiment, after a first set of multicellular signal data is collected, and a first transfer function for producing processed signals is developed, a second set of time varying stimulus is provided in combination with a patient controlled object, such as patient controlled object 713. During the time that the patient tries to mimic the motion of the system controlled target 712 with the visual feedback of the patient controlled target 713, and a second set of multicellular signal data is collected and a second, improved transfer function is produced by the system. Additional forms of feedback can be provided to the patient, such as tactile transducer 701 shown attached to patient 500's neck, and speaker 702 shown attached to processing unit third portion 130c fixedly mounted to the back of controlled wheelchair 310. Speaker 702 and tactile transducer 701 can provide feedback in the form of a time varying stimulus, a derivative of the multicellular signals, and/or a representation of the processed signals as controlled by patient 500

In a preferred embodiment, one or more system configuration routines can be performed without an operator, with the patient as the operator, or with an operator at a remote location such as when the system of the present invention is electronically connected with a computer or computer network such as the Internet. In another preferred embodiment, the patient training routine must be performed at least one time during the use of the system, preferably before patient 500 is given, by the system, full control of one or more controlled devices. For example, limited control of CPU 305 may include the ability to send and receive email but not the ability to adjust a computer-controlled thermostat. Limited control of wheelchair 310 may be to turn left or right, but not move forward or back, or to only allow travel at a limited velocity. For the purposes of this specification, limited control may also include no control of one or more controlled devices. Each controlled device will have different parameters limited by system 100 when patient 500 has not been given full control. In a preferred embodiment, the selection of these parameters; the values to be limited; the criteria for achieving full control such as the value of a success threshold achieved during a system configuration routine such as a patient training routine; and combinations of these, are modified only in a secured way such as only by a clinician utilizing electronic or mechanical keys or passwords.

In addition to successful completion of the patient training routine, completion of one or more other configuration routines may be required for patient 500 to have full control of one or more controlled devices, or multiple successful completions of a single routine. Success is preferably measured through the measurement of one or more performance parameters during or after the configuration routine. Success will be achieved by a performance parameter being above a threshold value, such as a threshold adjustable only by a clinician, such as a clinician at a remote site utilizing a password, a user identification, an electronic ID and/or a mechanical key. These configuration routines are utilized by the system to not only determine the applicability of full control to the patient, but to set or reset one or more system configuration parameters. System configuration parameters include but are not limited to: selection of cellular signals for processing by the processing unit; criteria for the selection of cells for processing; a coefficient of a signal processing function such as amplification, filtering, sorting, conditioning, translating, interpreting, encoding, decoding, combining, extracting, sampling, multiplexing, analog to digital converting, digital to analog converting, mathematically transforming; a control signal transfer function parameter such as a transfer function coefficient, algorithm, methodology, mathematical equation, a calibration parameter such as calibration frequency; a controlled device parameter such as a controlled device boundary limit; acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signals to patient; calibration parameter such as calibration duration and calibration frequency; controlled device parameter such as controlled device mode; alarm or alert threshold; and a success threshold.

As depicted in FIG. 3, operator 110 utilizes configuration apparatus 120 which includes two monitors, first configuration monitor 122a and second configuration monitor 122b, configuration keyboard 123, and configuration CPU 125, to perform a calibration routine or other system configuration process such as a patient training routine, algorithm and algorithm parameter selection and output device setup. The configuration routines, such as the patient training routine, include software programs and hardware required to perform the configuration. The embedded software and/or hardware may be included in the processing unit, such as processing unit second portion 130b, be included in selector module 400, be incorporated into configuration apparatus 120, a controlled device, or combinations of these. Configuration apparatus 120 may include additional input devices, such as a mouse or joystick, or an input device for a patient with limited motion, such as a tongue switch; a tongue palate switch; a chin joystick; a Sip n' Puff joystick controller; an eye tracker device; a head tracker device; an EMG switch such as an eyebrow EMG switch; an EEG activated switch; and a speech recognition device, all not shown.

Configuration apparatus 120 may include various elements, functions and data including but not limited to: memory storage for future recall of configuration activities, operator qualification routines, standard human data, standard synthesized or artificial data, neuron spike discrimination software, operator security and access control, controlled device data, wireless communication means, remote (such as via the Internet) configuration communication means and other elements, functions and data used to provide an effective and efficient configuration on a broad base of applicable patients and a broad base of applicable controlled devices. A system electronic ID can be embedded in one or more of the discrete components at the time, including an ID embedded at the time of system configuration. In an alternative embodiment, all or part of the functionality of configuration apparatus 120 is integrated into selector module 400 such that system 100 can perform one or more configuration processes such as a calibration procedure or patient training routine, utilizing selector module 400 without the availability of configuration apparatus 120.

In order to change a system configuration parameter, system 100 includes a permission routine, such as an embedded software routine or software driven interface that allows the operator to view information and enter data into one or more components of system 100. The data entered must signify an approval of the parameter modification in order for the modification to take place. Alternatively, the permission routine may be partially or fully located in a separate device such as configuration apparatus 120 of FIG. 3, or a remote computer such as a computer that accesses system 100 via the Internet or utilizing wireless technologies. In order to access the permission routine, and/or approve the modification of the system configuration parameters, a password or security key, mechanical, electrical, electromechanical or software based, may be required of the operator. Multiple operators may be needed or required to approve a parameter modification. Each specific operator or operator type may be limited by system 100, via passwords and other control configurations, to approve the modification of only a portion of the total set of modifiable parameters of the system. Additionally or alternatively, a specific operator or operator type may be limited to only approve a modification to a parameter within a specific range of values, such as a range of values set by a clinician when the operator is a family member. Operator or operator types, hereinafter operator, include but are not limited to: a clinician, primary care clinician, surgeon, hospital technician, system 100 supplier or manufacturer technician, computer technician, family member, immediate family member, caregiver and patient.

In a preferred embodiment, the system 100 of FIG. 3 includes an interrogation function, which interrogates the system to retrieve certain information such as on the demand of an operator. Based on the analysis of the information, a recommendation for a parameter value change can be made available to the operator, such as by automatic configuration or calibration routines that are initiated by the operator initiated interrogation function. After viewing the modification, the appropriate operator would approve the change via the permission routine, such as using a computer mouse to click "OK" on a confirmation box displayed on a display monitor, or a more sophisticated, password controlled methodology.

In a preferred embodiment, an automatic or semi-automatic configuration function or routine is embedded in system 100. This embedded configuration routine can be used in place of a configuration routine performed manually by Operator 110 as is described hereabove, or can be used in conjunction with one or more manual configurations. Automatic and/or semi-automatic configuration triggering event or causes can take many forms including but not limited to: monitoring of cellular activity, wherein the system automatically changes which particular signals are chosen to produce the processed signals; running parallel algorithms in the background of the one or more algorithms currently used to create the processed signals, and changing one or more algorithms when improved performance is identified in the background event; monitoring of one or more system functions, such as alarm or warning condition events or frequency of events, wherein the automated system shuts down one or more functions and/or improves performance by changing a relevant variable; and other methods that monitor one or more pieces of system data, identify an issue or potential improvement, and determine new parameters that would reduce the issue or achieve an improvement. In a preferred embodiment of the disclosed invention, when specific system configuration parameters are identified, by an automated or semi-automated calibration or other configuration routine, to be modified for the reasons described above, an integral permission routine of the system requires approval of a specific operator when one or more of the system configuration parameters are modified.

Operator 110 may be a clinician, technician, caregiver, patient family member or even the patient themselves in some circumstances. Multiple operators may be needed or required to perform a configuration routine or approve a modification of a system configuration parameter, and each operator may be limited by system 100, via passwords and other control configurations, to only perform or access specific functions. For example, only the clinician may be able to change specific critical parameters, or set upper and lower limits on other parameters, while a caregiver, or the patient, may not be able to access those portions of the configuration procedure or the permission procedure. The configuration routine includes the setting of numerous parameters needed by system 100 to properly control one or more controlled devices. The parameters include but are not limited to various signal conditioning parameters as well as selection and de-selection of specific multicellular signals for processing to generate the device control creating a subset of signals received from the sensor to be processed. The various signal conditioning parameters include, but are not limited to, threshold levels for amplitude sorting, other sorting and pattern recognition parameters, amplification parameters, filter parameters, signal conditioning parameters, signal translating parameters, signal interpreting parameters, signal encoding and decoding parameters, signal combining parameters, signal extracting parameters, mathematical parameters including transformation coefficients and other signal processing parameters used to generate a control signal for transmission to a controlled device.

The configuration routine will result in the setting of various system configuration output parameters, all such parameters to be considered system configuration parameters of the system of the present invention. Configuration output parameters may include but are not limited to: electrode selection, cellular signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In a preferred embodiment, the configuration output parameters are stored in memory in one or more discrete components, and the parameters are linked to the system's unique electronic ID.

Calibration, patient training, and other configuration routines, including manual, automatic and semi-automatic routines, may be performed on a periodic basis, and may include the selection and deselection of specific cellular signals over time. The initial configuration routine may include initial values, or starting points, for one or more of the configuration output parameters. Setting initial values of specific parameters, may invoke a permission routine. Subsequent configuration routines may involve utilizing previous configuration output parameters that have been stored in a memory storage element of system 100. Subsequent configuration routines may be shorter in duration than an initial configuration and may require less patient involvement. Subsequent configuration routine results may be compared to previous configuration results, and system 100 may require a repeat of configuration if certain comparative performance is not achieved.

The configuration routine may include the steps of (a) setting a preliminary set of configuration output parameters; (b) generating processed signals to control the controlled device; (c) measuring the performance of the controlled device control; and (d) modifying the configuration output parameters. The configuration routine may further include the steps of repeating steps (b) through (d). The configuration routine may also require invoking a permission routine.

In the performance of a configuration routine, the operator 110 may involve patient 500 or perform steps that do not involve the patient. In the patient training routine and other routines, the operator 110 may have patient 500 imagine one or more particular movements, imagined states, or other imagined events, such as a memory, an emotion, the thought of being hot or cold, or other imagined event not necessarily associated with movement. The patient participation may include the patient training routine providing one or more time varying stimulus, such as audio cues, visual cues, olfactory cues, gustatory cues, tactile cues, moving objects on a display such as a computer screen, moving mechanical devices such as a robotic arm or a prosthetic limb, moving a part of the patient's body such as with an exoskeleton or FES implant, changing audio signals, changing electrical stimulation such as cortical stimulation, moving a vehicle such as a wheelchair or car; moving a model of a vehicle; moving a transportation device; and other sensory stimulus. The imagined movements may include the imagined movement of a part of the body, such as a limb, arm, wrist, finger, shoulder, neck, leg, angle, and toe, as well as imagining moving to a location, moving in a direction and moving at a velocity or acceleration.

Referring back to FIG. 3, the patient imagines moving system controlled target 712 along planned trajectory 711, as target 712 is moving as controlled by the system or manually by an operator. The current processed signal, hereinafter a representation of the processed signal, available by applying a transfer function to the multicellular signals detected during the imagined movement or other step of the patient training routine, is displayed in the form of control of patient controlled target 713. The transfer function is preferably based on multicellular signals stored during a previous imagined movement, or multiple previous imagined movements, preferably two or more sets of states of time varying stimulus. The representation of the processed signals may mimic the time varying stimulus, similar to patient controlled object 713 being a similar form to system controlled object 712. Alternatively, the time varying stimulus and representation of the processed signals may take different forms, such as a time varying stimulus comprising an object on a visual display, wherein the representation comprises a moving mechanical structure, or the stimulus being a moving mechanical structure and the representation comprising an object on a visual display. The representation of the processed signals can be provided to the patient in visual form such as a visual representation of limb motion displayed on a computer monitor, or in one or more sensory forms such as auditory, olfactory, gustatory, and electrical stimulation such as cortical stimulation. The representation of the processed signals can be provided in combinations of these and other forms.

In a preferred embodiment, the first patient training step does not include patient controlled object 713 or it includes a patient controlled target whose processed signals are not based on a set of multicellular signals collected during a previous imagined movement. Multiple steps of providing a set of states of the time varying stimulus and recording the multicellular signal data may involve different subsets of cells from which the multicellular signals are detected. Also, different sets of states of time varying stimulus may have different numbers of cells in each. Alternative to the system controlled target 712 along planned trajectory 711, the patient may imagine movements while viewing a time varying stimulus comprising a video or animation of a person performing the specific movement pattern. In a preferred embodiment, this visual feedback is shown from the patient's perspective, such as a video taken from the person performing the motion's own eye level and directional view. Multiple motion patterns and multiple corresponding videos may be available to improve or otherwise enhance the patient training process. The patient training routine temporally correlates a set of states of the time varying stimulus with the set of multicellular signal signals captured and stored during that time period, such that a transfer function can be developed for future training or controlled device control. Correlations can be based on numerous variables of the motion including but not limited to: position, velocity and acceleration of the time varying stimulus; a patient physiologic parameter such as heart rate; a controlled device parameter; a system environment parameter; a password controlled parameter; a clinician controlled parameter; and a patient training routine parameter. In the patient training routine of FIG. 3, the controlled device, CPU 305 and controlled monitor 302 are used in the patient training routine to display the time varying stimulus as well as the representation of the processed signal. In a subsequent step, wheelchair 310 can also be employed, such as by a system controlling the wheelchair while the patient imagines the control, the wheelchair movement being the time varying stimulus.

During the time period that a set of states of the time varying stimulus is applied, multicellular signal data detected by the implanted sensor is stored and temporally correlated to that set of states of the time varying stimulus provided to the patient. In a preferred embodiment, the system of the present invention includes a second patient training routine and a second controlled device, wherein the first patient training routine is used to configure the first controlled device and the second patient training routine is used to configure the second controlled device. The two patient training routines may include different time varying stimulus, chosen to optimize the routine for the specific controlled device, such as a moving cursor for a computer mouse control system, and a computer simulated prosthetic limb for a prosthetic limb control system. In a preferred system, the first controlled device is a prosthetic arm and the second controlled device is a prosthetic leg, this system having two different time varying stimulus in the two corresponding patient training routines. In another preferred system, the first controlled device is a prosthetic arm and the second controlled device is a wheelchair, this system also having two different time varying stimulus in the two corresponding patient routines. In an alternative, preferred embodiment, a controlled device surrogate is utilized in the patient training routine. The controlled device surrogate preferably has a larger value of one or more of: degrees of freedom; resolution; modes; discrete states; functions; and boundary conditions. Numerous boundary conditions with greater values for the surrogate device can be employed, such boundary conditions as: maximum distance; maximum velocity; maximum acceleration; maximum force; maximum torque; rotation; and position. The surrogate device employing larger values of these parameters creates the scenario wherein the patient is trained and/or tested with a device of more complexity than the eventual controlled device to be used.

The time varying stimulus may be supplied to the patient in numerous forms such as visual, tactile, olfactory, gustatory, and electrical stimulation such as cortical stimulation. The time varying stimulus may be moved around manually, automatically produced and controlled by a component of the system such as the processing unit, or produced by a separate device. The time varying stimulus may include continuous or semi-continuous motion of an object, such as an object moving on a visual display, a mechanical object moving in space, or a part of the patient's body moving in space. The time varying stimulus may be of a short duration, such as an object appearing and disappearing quickly on a display, or a flash of light.

In a preferred embodiment, the patient training routine includes multiple forms of feedback, in addition to the time varying stimulus, such feedback provided to the patient in one or more forms including but not limited to: visual; tactile; auditory; olfactory; gustatory; and electrical stimulation. The additional feedback may be a derivative of the multicellular signals, such as visual or audio feedback of one or more neuron spike modulation rates. Different forms of feedback may be provided as based on a particular device to be controlled by the processed signals. Numerous parameters for the time varying stimulus and other feedback may be adjustable, such as by the operator or patient, these parameters including but not limited to: sound volume and frequency; display brightness, contrast, size and resolution; display object size; electrical current parameter such as current or voltage; mechanical or visual object size, color, configuration, velocity or acceleration; and combinations of these.

A configuration routine such as a calibration or patient training routine will utilize one or more configuration input parameters to determine one or more system output parameters used to develop a processed signal transfer function. In addition to the multicellular signals themselves, system or controlled device performance criteria can be utilized. Other configuration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including but not limited to modulation of any signal property. Additional configuration input parameters include but are not limited to: system performance criteria, controlled device electrical time constants, controlled device mechanical time constants, other controlled device criteria, types of electrodes, number of electrodes, patient activity during configuration, target number of signals required, patient disease state, patient condition, patient age and other patient parameters and event based (such as a patient imagined movement event) variations in signal properties including neuron firing rate activity. In a preferred embodiment, one or more configuration input parameters are stored in memory and linked to the embedded, specific, unique electronic identifier. All configuration input parameters shall be considered a system configuration parameter of the system of the present invention.

It may be desirous for the configuration routine to exclude one or more multicellular signals based on a desire to avoid signals that respond to certain patient active functions, such as non-paralyzed functions, or even certain imagined states. The configuration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor. In a preferred embodiment, an automated or semi-automated calibration or other configuration routine may include through addition, or exclude through deletion, a signal based on insufficient activity during known patient movements.

The configuration routines of the system of the present invention, such as a patient training routine in which a time varying stimulus is provided to the patient, may conduct adaptive processing, such as adapting between uses or within a single patient training routine. The adaptation may be caused by a superior or inadequate level of performance, as compared to a threshold value, such as an adjustable threshold. In a preferred embodiment, performance during a patient training routine above a threshold value causes the duration of the routine to decrease, and performance below a threshold value causes the duration of the routine to increase. Control of the controlled device or surrogate controlled device is a preferred way of measuring performance. Alternatively, a change in multicellular signals, such as a change in modulation rate may cause an adaptation to occur. A monitored difference is a first patient training event and a second patient training event, such as a difference in signal modulation, may cause an adaptation in the patient training routine, such as to preferentially choose one time varying stimulus over another time varying stimulus. Other causes include a change to a patient parameter, such as the level of patience consciousness. In a preferred embodiment, at a low level of consciousness, the patient training routine changes or discontinues. The level of consciousness may be determined by the multicellular signals detected by the sensor. Alternatively, the level of consciousness can be detected utilizing a separate sensor, such as a sensor to detect EEG or LFP signals. The patient training routine may adapt automatically, such as due to a calculation performed by the processing unit, or may adapt due to operator input.

The systems of the present invention, such as system 100 of FIG. 3, include a processing unit that processes multicellular signals received from patient 500. Processing unit second portion 130*b* and other processing unit components, singly or in combination, perform one or more functions. The functions performed by the processing unit include but are not limited to: producing the processed signals; transferring data to a separate device; receiving data from a separate device; producing processed signals for a second controlled device; activating an alarm, alert or warning; shutting down a part of or the entire system; ceasing control of a controlled device; storing data and performing a configuration.

In order for the processing unit of system 100 to perform one or more functions, one or more system configuration parameters are utilized. These parameters include pieces of data stored in, sent to, or received from, any component of system 100, including but not limited to: the sensor; a processing unit component; processing unit second portion 130*b*; or a controlled device. Parameters can be received from devices outside of system 100 as well, such as configuration apparatus 120, a separate medical therapeutic or diagnostic device, a separate Internet based device or a separate wireless device. These parameters can be numeric or alphanumeric data, and can change over time, either automatically or through an operator involved configuration or other procedure.

The processing unit, or other component of system 100 may produce multiple processed signals for controlling one or more controlled device. This second processed signals may be based on multicellular signals of the sensor, such as the same set of cells as the first processed signals are based on, or a different set of cells emanating signals. The signal processing used to produce the additional processed signals can be the same as the first, or utilize different processing, such as different transfer functions. Transfer functions may include different algorithms, coefficients such as scaling factors, different types of feedback, and other transfer function variations. Alternatively, the additional processed signals may be based on signals not received from the sensor in which the first processed signals are derived. An additional sensor, such as a similar or dissimilar sensor, may provide the signals to produce the additional processed signals, or the system may receive a signal from an included input device such as a tongue switch; tongue palate switch; chin joystick; Sip n' Puff joystick controller; eye gaze tracker; head tracker; EMG switch such as eyebrow EMG switch; EEG activated switch; speech recognition device; and combinations thereof. The additional processed signals may be derived from a monitored biological signal such as a signal based on eye motion; eyelid motion; facial muscle activation or other electromyographic activity; heart rate; EEG; LFP; respiration; and combinations thereof. In creating the additional processed signals, the processing unit may convert these alternative input signals into a digital signal, such as a digital signal used to change the state of the system, such as a change in state of an integrated configuration routine.

Figure 4A:
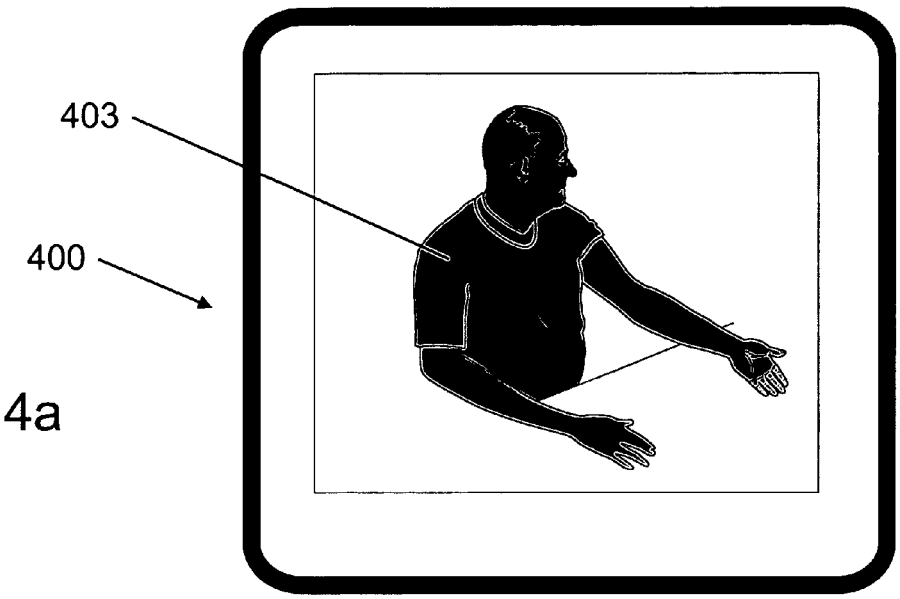
FIG. 4a illustrates a patient training display with a representation of a human figure including an open fist time varying stimulus, consistent with the present invention.
Figure 4B:
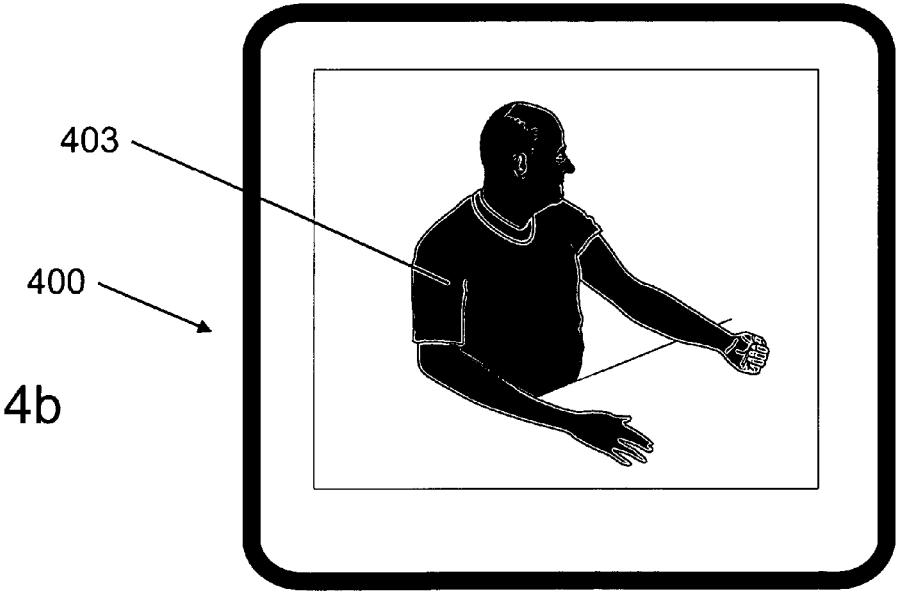
FIG. 4b illustrates a patient training display with a representation of a human figure including an open fist time varying stimulus, consistent with the present invention.

Referring now to FIG. 4a and FIG. 4b, the patient training display including the representation of a human figure of the present invention is illustrated. Module 400 is a visual display, such as a color LCD display or a touch screen monitor. Module 400 displays a human figure in the form of a computer generated image of a man. In FIG. 4a, the man is depicted with both arms on a surface such as a desk, with the left hand in an open fist, palm up configuration. FIG. 4b depicts the same man at the desk, and the only change is the left hand is now in a closed fist configuration. Human FIG. 403 may have been presented in the form of a continuous motion animation such that the patient performing the patient training routine or the system troubleshooting routine sees the continuous change in the hand such as the curling in of the fingers. Alternatively, human FIG. 403 may be presented in the form of discrete images, such as the two images of FIG. 4a and FIG. 4b. In a preferred embodiment, the patient or other operator, utilizing the patient input switch or other type of input device described in detail hereabove, may change one or more properties of human FIG. 403. In one embodiment, the gender can be changed from the man of FIG. 4a and FIG. 4b to a woman. In another embodiment, the relative age of the man in FIGS. 4a and 4b may also be changed. In yet another embodiment, the side of the body of the limbs used, such as changing from the left to the right hand in FIG. 4a and FIG. 4b, can be accomplished.

Module 400 may include one or more speakers, not shown, to provide audio feedback such as a time varying stimulus including audible information. The audio feedback may include spoken language, such as spoken words that can be presented in one or more languages as selected by the patient or other operator of the system. Multiple other forms of feedback can be provided to the patient, such as via transducers integral to module 400 or implanted in or attached to the patient. These transducers can provide feedback is a form selected from the group consisting of: visual; tactile; auditory; gustatory; olfactory; taste; electrical stimulation; and combinations thereof. In an alternative embodiment, visual images, such as camera pictures or continuous images from a video camera, can be used in addition or alternative to the computer images of FIG. 4a and FIG. 4b. One or more actors and/or actresses can be used, such as actors selected from multiple genders, age groups, nationalities, spoken language type, and other variations, the actors performing multiple human body movements and was as other tasks presented in visual form to the patient in the performance of the patient training routine or system troubleshooting of the present invention.

Figure 5:
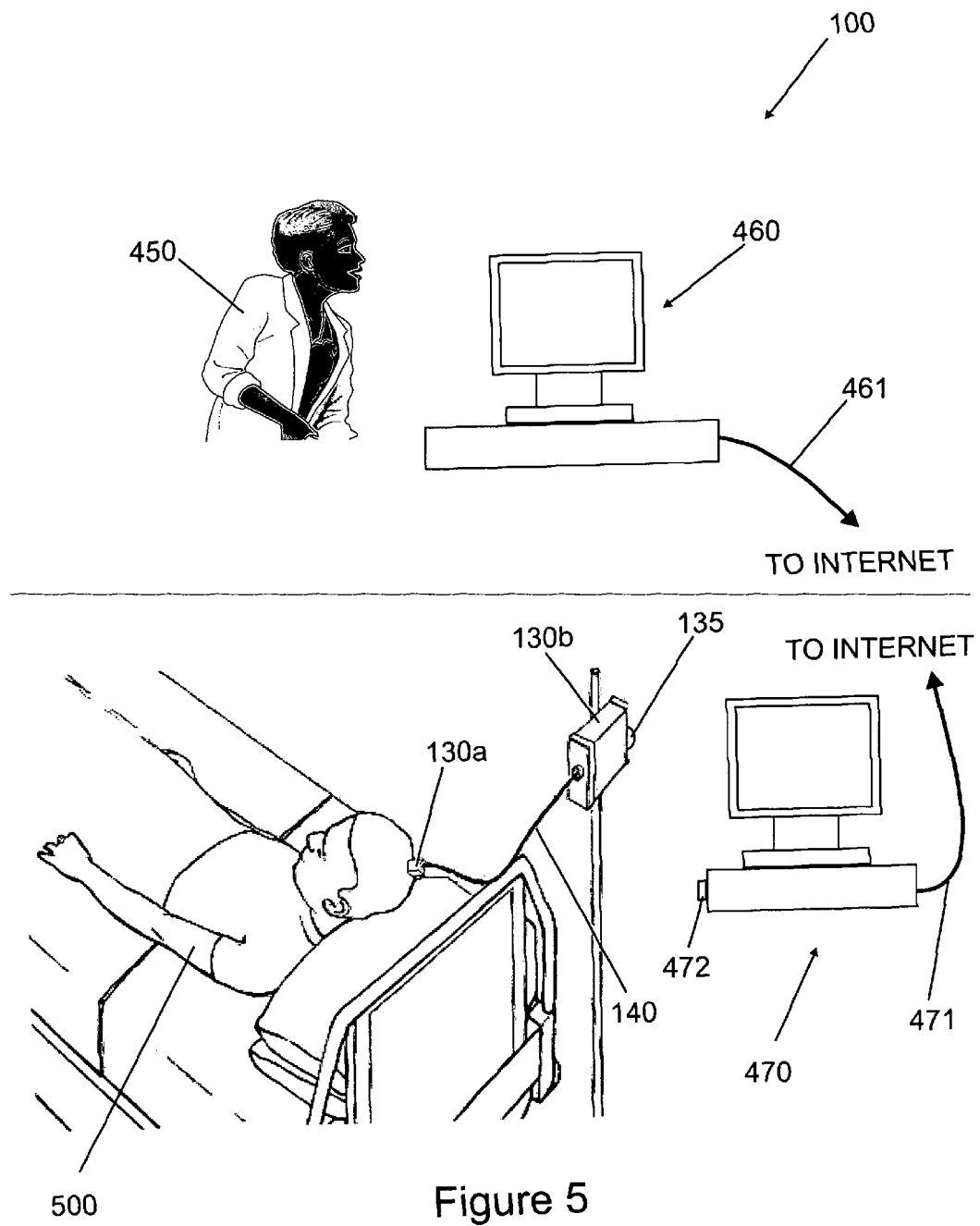
FIG. 5 illustrates a biological interface system consistent with the present invention wherein the patient undergoes a patient training routine while a remote operator assists in the procedure.

Referring now to FIG. 5, another preferred embodiment of the present invention is illustrated in which a biological interface system includes an integrated patient training routine and/or a system troubleshooting routine. The patient training routine or system troubleshooting routine is conducted with an operator, such as a technician or healthcare worker. This operator is at a location remote from the patient and uses a remote access routine that provides data transfer means to allow the remote operator to send and/or receive data to or from one or more system components. The patient training routine and/or system troubleshooting routine can be conducted with patient involvement, or may be performed wherein the patient is unaware of the remote operator. The patient training routine and/or system troubleshooting routine is performed to generate one or more system configuration parameter values. In a preferred embodiment, the system configuration parameters generated are used to create a transfer function used by the processing unit to apply to the multicellular signals to produce processed signals transmitted to one or more devices to be controlled.

Patient 500 has been implanted with a sensor, not shown, such as a sensor implanted in the motor cortex of the patient's brain. Processing unit first portion 130a is removably attached to a connector on the patient's skull, connector not shown, which is electrically attached to each of the electrodes of the implanted sensor. Patient 500 may utilize an input device, not shown, such as a tongue switch and/or other input device described in detail hereabove. The patient input device can be used to perform one or more functions integral to the patient training routine and/or system troubleshooting routine. Processing unit first portion 130a transmits signals to processing unit second portion 130b via intra-processing unit cable 131. Processing unit second portion 130b transmits signals to a controlled device, patient computer 470 via wireless transceiver 135 of processing unit second portion 130b and transceiver 472 of patient computer 470. Cable 131 includes one or more of electrical conduits and fiber optic conduits. In alternative embodiments, cable 131 is eliminated through the use of wireless communication means, such as RF communication means.

Patient computer 470 is positioned in a location such that the patient can visualize the video monitor of patient computer 470 and the visual representation of the human figure of the present invention can be provided to the patient. In a preferred embodiment, the patient imagines one or more movements or imagined states, while the human figure is provided, such that a set of multicellular signals can be detected and stored in system memory, this set of data is used to generate one or more system configuration parameters. Patient computer 470 can have one or more functions, such as cursor, keyboard, joystick, mouse, or other input device control, controlled by the processed signals of system 100. Patient computer 470 may include a portion of the processing unit, such that final signal processing is performed by the electronics of patient computer 470. In an alternative embodiment, patient computer 470 incorporates all of the functions of processing unit second portion 130b, which is then eliminated. In addition, patient computer 470 may be a surrogate or intermediate for another controlled device such that patient 500 utilizes patient computer 470 to control a separate external device such as a robot, a thermostat or numerous other devices controllable through a computer interface. In addition, patient computer 470 may function, in whole or in part, as the system configuration apparatus, such as configuration apparatus 120 of FIG. 3, thus reducing the need for multiple computers, computer monitors, etc.

Patient computer 470 is attached to the Internet via communication means 471. In alternative embodiments patient computer 470 may be alternatively or additionally attached to a different network of computers, such as a local group of computers, a LAN, a WAN, a WIFI connection, or other single or group of computers or other electronic devices in proximity to or remote from the patient's location. Computer communication means 471 may include one or more of a phone cable and modem, a cable modem, a network routing device, a wireless transmission device, a wireless phone and/or other communication device and/or conduit. In an alternative embodiment, a second remote operator at a third location is required to complete the patient training routine or the system troubleshooting routine of the present invention.

As depicted in FIG. 5, system 100 further includes technician computer 460, a separate computer at a location remote from patient 500 such as a hospital or service center of the manufacturer or provider of system 100. Utilizing technician computer 460 is technician operator 450, an operator of the biological interface system 100 of the present invention. Technician operator 450 is knowledgeable of system 100. Technician operator 450 uses technician computer 460 to access patient computer 470 such as via the Internet utilizing computer communication means 461. Through patient computer 470, one or more components of system 100 can be accessed such as processing unit second portion 130b, processing unit first portion 130a and potentially the sensor, not shown.

The remote access provided in system 100 of FIG. 5 is beneficial in allowing the patient training routine and/or system troubleshooting routine of the present invention to be performed by a remote operator, avoiding the need to visit patient 500's location. Other system configuration routines such as those that result in calibrations, other system improvements, and other parameter modifying events may be performed while one or more operators are at a remote location. In a preferred embodiment, technician operator 450 approves one or more system configuration parameter values that are set or modified, utilizing system 100's permission routine. Prior to making the approval, technician operator 450 may run one or more tests, with or without patient involvement, and approve the modification only upon successful results from those tests.

Nurse groups, clinical care organizations, clinical research organizations, rehabilitation groups, health care financial providers such as Blue Cross and other applicable groups may access the system for the benefit of the patient, the health care system or both. System 100 of the present invention can be configured to allow a single or multiple operators, these operators located at the patient site, remotely or both, to change one or more system configuration parameters utilized by the processing unit to perform a function. Integrated into one or more components of system 100 is a permission routine that requires an operator, such as technician operator 450 of FIG. 5, to provide an approval of the modification of one or more parameters. The permission routine can be implemented through the use of technician computer 460 wherein technician operator 450 uses an input device such as a mouse or keyboard to enter information confirming the acceptability of the change. Each parameter modification may be linked with one or more healthcare fees, such as a clinician fee wherein the operator performing the patient training routine or system troubleshooting routine of the present invention is a clinician. In a preferred embodiment, system 100 records these billable events and makes them available to technician operator 450 on demand.

There may be various reasons for the patient training routine or system troubleshooting routine to be performed. The resultant system configuration parameter modifications may improve performance, safety, longevity of use such as battery life, allow additional external devices to be controlled, and other progressive changes in a complex system. These routines may be invoked due to one or more of the following: adaptive processing of the system; alarm or warning condition; a change in patient performance; a change in patient condition; a cellular signal change such as a modulation change; the initial setting of a system configuration parameter; adding a new device to be controlled, such as when adequate performance is achieved during a test; and removal of a controlled device such as when inadequate performance has been identified.

In a preferred embodiment, the permission routine includes one or more embedded software routines which link specific operator approval with changes to specific parameters, such as via a lookup table stored in electronic memory. One or more computers or other data entry devices are used by system 100 to perform the permission routine. In a preferred embodiment, a dialog box appears on the monitor of technician computer 460 including the parameter description, current value, proposed new value, and an "OK" box that the clinician clicks with the mouse to approve the change. Approval can be signified by typing a code on one or more keyboards or other text entry devices in communication with the system, clicking or otherwise activating a specific icon on a display, clicking a mouse at one or more specific locations on a display, and entering approval data via spoken voice into a voice recognition system. In an alternative embodiment, a second confirmation, such as an "ARE YOU SURE" dialog box, is utilized after a first approval. In another alternative embodiment, the operator can approve multiple parameter modifications with a single action, such as a confirmatory mouse click. In another alternative embodiment, approval is required by two or more operators. In another alternative embodiment, the permission routine requires the operator to perform a task, such as entering a security code, performing a system test, performing a patient task such as control of a controlled device with modified parameters, or other task prior to or in conjunction with approving the parameter change with one of the various means described above.

System configuration parameters can be stored within one or more components of system 100, transmitted from one or more components of system 100 or received by one or more components of system 100. System configuration parameters can include the various patient specific values, coefficients and other variables that are set and/or changed in the performance of the patient training routine or system troubleshooting routine of the present invention. System configuration parameters include spike sorting variables such as amplitude threshold variables. System configuration parameters can include signal processing variables such as sampling rate by signal, sampling rate by group of signals, amplification by signal, amplification by group of signals, filter parameter by signal, filter parameter by group of signals, sorting variable, conditioning variable, translating variable, interpreting variable, encoding variable, decoding variable, extracting variable, mathematical transformation variable, signal to noise ratio variable, frequency of signal variable, amplitude of signal variable, neuron firing rate variable, standard deviation in neuron firing rate variable and modulation of neuron firing rate variable. System configuration parameters may include signal selection variables including but not limited to: electrode selection variable, cellular signal selection variable, neuron spike selection variable, electrocorticogram signal selection variable, local field potential selection variable and electroencephalogram signal selection variable.

System configuration parameters may also include one or more controlled device parameters including but not limited to: allowed devices that the patient can control; unique ID for device such as that used by a handshaking protocol in order to achieve secure and accurate signal transfer; parameter indicating partial control of a multi-function device; movement parameter of device; a position, velocity, acceleration, torque, direction and/or momentum variable of a device such as a maximum velocity parameter; a power parameter; a therapeutic device parameter such as dose amount, time for start of dose, rate of dose, duty cycle of dose and amount of energy such as stimulation energy; mechanical time constant variable and electrical time constant variable. Additional system configuration parameters may also include: a list of permissions for specific operator or operator types; operator usernames; operator passwords; on or off variables; system reset parameters; maximum on time of system parameters and allowable times of day for system use by the patient.

Additional system configuration parameters may include calibration parameters including but not limited to: electrode selection; cellular signal selection; neuron spike selection; electrocorticogram signal selection; local field potential signal selection; electroencephalogram signal selection; sampling rate by signal; sampling rate by group of signals; amplification by signal; amplification by group of signals; filter parameters by signal and filter parameters by group of signals; patient-activity during calibration; target number of signals required; patient disease state; patient condition; patient age and other patient parameters. Additional system configuration parameters may include system performance criteria including but not limited to: target number of signals required; patient disease state; patient condition; patient age and other patient parameters. Additional system configuration parameters include but are not limited to: algorithm selection parameter; group of mathematical algorithms parameter; information upload command; information download command; alarm, warning or alert parameter; criteria to determine adequate performance of system; failure threshold parameter.

Numerous protection schemes can be included in system 100 to prevent unauthorized representation of a user including but not limited to password schemes, IP address confirmation, operator ID hardware such as fingerprint or retinal scan identification hardware as well as electromechanical and mechanical keys. In a preferred embodiment, system 100 further comprises an operator validation routine, using the measures listed above and other measures to confirm the identification of one or more operators. In another preferred embodiment, the system includes a login function, wherein each operator enters one or more of a user name, a user group, a user ID and a password. The login function may ensure that a mechanical or electronic key is in place at a specific port on the system, not shown. The login function may upload various pieces of information, such as from a remote computer, including IP address, electronic key information, computer login information and other information.

Permission routines may be required by a second operator, such as when a first operator determines a system configuration parameter to be changed, a second operator must confirm the acceptability of the change. Numerous alternatives can be anticipated by those skilled in the art, without departing from the spirit and scope of this application, wherein one or more operators are required by the system to approve a modification to a system configuration parameter. In some instances, the parameter may remain unchanged until the approval is received, while in other instances a temporary period, such as a tryout period, may use the system with the parameter modified, requiring the approval to maintain the modification for an extended period of time.

Numerous operators can be defined as applicable to system 100 including but not limited to clinicians, caregivers, care providers, technicians, patient family members and the patients themselves. A matrix of permission parameters can be included in system 100 such that specific parameter modifications can only be modified and/or approved by particular operators. Defined levels for operators and operator groups can be established to control certain groups of parameters. Alternatively or additionally, the value ranges, within which certain parameters can be modified, can also be operator specific. In a preferred embodiment, a limited, or relatively small number of parameters can be approved for modification by the patient.

In a preferred embodiment, the system 100 of FIG. 5 includes an interrogation function that interrogates the system to retrieve certain information. Based on the analysis of the information, a recommendation for a patient training routine or system troubleshooting routine of the present invention may be indicated and/or required. In another preferred embodiment, system 100 of FIG. 5 includes a test routine. The test routine can be run any time by an operator, at the patient site or remotely, in determining whether or not a parameter should be changed, in determining the final value for the change, or to confirm or otherwise test the change. For certain parameters, in addition to the approval required by the permission routine, system 100 may require the test routine be run. In yet another preferred embodiment, a successful performance during the test is also required for parameter modification.

In another preferred embodiment, the system 100 of FIG. 5 further comprises a monitoring routine. The monitoring routine is used by system 100 to automatically monitor system performance and other system parameters and provide, to one or more operators, a recommendation for modifying one or more of the system configuration parameters used by the processing unit, such as processing unit first portion 130a and/or processing unit second portion 130b, to perform a function. The recommendation will include the identification of a system configuration parameter to be modified, but may also include a recommendation or requirement to perform the patient training routine or system troubleshooting routine of the present invention. The recommendation can be based on an analysis of real time or historic data, including cellular signals such as neural signals, and other information. In a preferred embodiment, the monitoring routine modifies the parameter for a limited time period without operator approval, such as to allow the patient limited control of the controlled device, such as to communicate via system 100, potentially to a technician about an issue requiring the parameter modification. At a predetermined time, the parameter modification may revert back or the system performance may be otherwise modified such as ceasing control of one or more controlled devices. The monitoring routine includes software embedded in one or more components of system 100 that perform the analysis and monitoring. The monitoring routine may get information from the sensor of system 100 as well as other physiologic and non-physiologic sensors, such as sensors monitoring the patient, the system environment, and/or the controlled device. The monitoring routine may itself include one or more system configuration parameters, such as those requiring operator approval via the permission routine of the present invention. The monitoring routine may involve an analysis of raw cellular signal information, processed, or a derivative of the cellular signal information, controlled device information, patient physiologic information, environment information and other information.

In another preferred embodiment, system 100 includes a system configuration parameter modification notification function, preferably activated automatically by the system, which notifies an operator, or multiple operators, of a suggested or pending change. The notification function may require that the parameter modification be made, and potentially tested, before performing the notification function. The system configuration parameter modification notification function may be initiated by the monitoring function, calibration functions and configuration functions described in detail hereabove. The notification to the operator can take the form of one or more of: audible alert; a visual alert; olfactory cues; tactile feedback; email; phone call or message; and other information sent via wired and wireless means. Modification of certain parameters that have been notified to the operator by the notification function will require approval of the operator via the permission routine. This approval may be required before the parameter is modified, or a short time thereafter. The operator may perform a test, or may be required to perform a test, to confirm acceptability of the modification.

In another preferred embodiment, system 100 further comprises a patient confirmation routine, such as a software routine embedded in one or more components of system 100. The patient confirmation routine requires that the patient, after temporarily controlling the device with new values for one or more system configuration parameters, confirm the acceptability of these modifications. After the acceptability has been confirmed, continuous or long-term full control of the controlled device with the now tested parameter modifications is provided.

In situations where patient 500 may be at a location remote from caregivers or family members, it may be desirous for system 100 to include a means for a disabled patient to turn on or off one or more components of system 100, or even reset the system. Switches that control these functions can be driven by eye motion, eyelid motion, facial muscle motion or other electromyographic activity. Alternatively, the switches could be driven by neural information or processed neural information, such as a timecode of brain activity.

Figure 6:
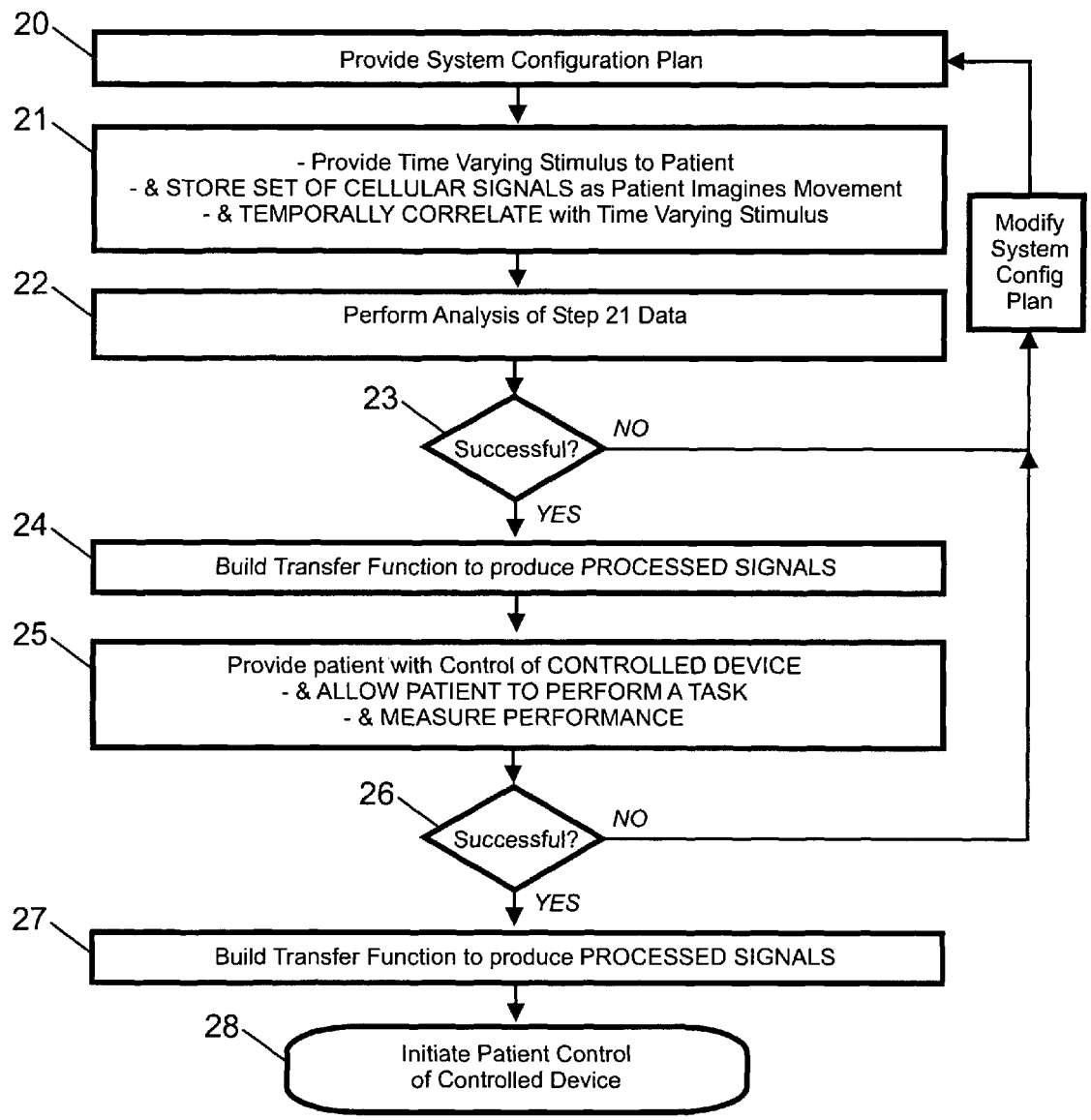
FIG. 6 illustrates a patient training routine flow chart of an exemplary embodiment of a biological interface system consistent with the present invention wherein a configuration plan may be improved prior to requiring the patient to control a device.

Referring now to FIG. 6, a flow chart of the patient training routine of an additional embodiment of the biological interface system of the present invention is illustrated comprising multiple steps and conditional statements that determine the progression from step to step. The patient training routine is included in a software program or module embedded in one or more components of the system such as the processing unit. Alternatively, an additional component is included in the system, such as a computer system used to configure the system, and the patient training routine, or a portion of the patient training routine is embedded in whole or in part in the additional component. The patient training routine may be activated automatically by the system, or an operator of the system, such as the patient's clinician or the patient themselves, may initiate and/or conduct the patient training routine.

Referring back to FIG. 6, Step 20 includes the patient training routine providing to the patient a series of steps whose order and tasks make up a system configuration plan. Step 21 includes providing to the patient a set of states of a time varying stimulus. The time varying stimulus can provide a target for a patient's imagined movement and/or simply be a trigger to initiate the imagined movement or other imagined state. The time varying stimulus can be provided in multiple forms such as: visual; tactile; auditory; olfactory; gustatory; electrical stimulation such as cortical stimulation; and combinations thereof. The time varying stimulus may be provided in many different types such as: computer icon; visual display object such as the visual representation of the human figure as described in reference to FIG. 1; moveable mechanical assembly such as a robotic arm; vehicle such as a wheelchair; single or multi-frequency sound; stimulation electrode such as cortical stimulation electrode; robot or robotic component; tactile transducer such as vibrating skin patch; and combinations thereof. The time varying stimulus can include continuous or semi-continuous motion such as an icon moving on a computer screen. The time varying stimulus can include a mechanical object moving in space, such as a robotic arm or a prosthetic limb. The time varying stimulus can be provided via one or more controlled devices of the system, such as an exoskeleton device or FES device moving one of the patient's own limbs. The time varying stimulus may be provided as a short duration stimulus, such as an object that appears on a visual display for less than one second, or a brief flash of light.

In a preferred embodiment, the time varying stimulus has an adjustable parameter, such as a parameter adjustable in a secured manner such as via the permission routine described hereabove. One or more parameters of the time varying stimulus may have a range of applicable values, such as a range of position of a cursor or human figure on a computer screen, and these types of ranges may be an adjustable parameter. Other adjustable parameters include but are not limited to: display brightness or contrast; display size; display resolution; electrical current parameter such as current or voltage; object velocity, acceleration and position; object size and color; sound volume; sound frequency; tactile sensor force, frequency and pulse width; and combinations thereof. The adjustment to a time varying stimulus parameter may be accomplished by one or more components of the system, such as the processing unit. The adjustment may be accomplished by one or more users of the system, such as the patient utilizing an input device as has been described hereabove.

Referring back to FIG. 6, Step 21 further includes the step of recording and storing, such as in electronic memory of a system component such as the processing unit, a first set of multicellular signals simultaneous with the patient imagining a movement associated with the provided set of states of the time varying stimulus. In a preferred embodiment, in a previous step, not shown, the patient has viewed the set of states of the time varying stimulus at least one time prior to the recording of the first set of multicellular signals. The first set of cellular signals are correlated, or mapped, to the set of states of the time varying stimulus. The correlation can be synchronized in time, called temporal mapping, or correlated to another parameter including but not limited to: a patient physiologic parameter such as heart rate; a controlled device parameter; a system environment parameter; a password controlled parameter; a clinician controlled parameter; a patient training routine parameter; and combinations thereof. In addition to the sensor detecting the multicellular signals, one or more additional sensors can be incorporated into the system. These sensors can be selected from the group consisting of: EKG sensor; respiration sensor; blood glucose sensor; temperature sensor; blood pressure and other pressure sensors; EEG sensor; perspiration sensor; cellular signal activity including neural activity sensor; skin conductance and other impedance sensor; strain gauge; light sensor; and combinations thereof. Numerous types of data can be collected and correlated to the time varying stimulus such as: patient physiologic data; object or patient motion data including data collected from a video recording device; system environment data; controlled device data; and other data. Patient physiologic data can be selected from the group consisting of: EKG; respiration; blood glucose; temperature; blood pressure; EEG; perspiration; cellular signal activity including neural activity; skin conductance; and combinations thereof. In an alternative embodiment, step 21 includes the recording of patient or other data without the providing of a time varying stimulus. In another alternative embodiment, step 21 does not include correlating the stored data with the time varying stimulus.

Step 22 includes an analysis of one or more sets of data that are collected during step 21, such as the multicellular signals, other patient physiologic data, one or more time varying stimulus sets of data, and other data. The analysis may require controlled device data such as time constant data, input level data such as range of a parameter value data; output level data such as boundary condition data; alarm condition data; and combinations thereof. The analysis produces one or more outputs to be utilized in Step 23. In a preferred embodiment, the data analyzed is selected from the group consisting of: cell sorting data such as spike sorting data; cellular signal modulation rates including modulation rates for a group of cells such as the group used to produce the processed signals; a count of neural spikes; heart rhythm data; skin conductance data; respiration data; and combinations thereof.

Step 23 includes the comparison of the one or more outputs of the analysis of step 22 to one or more corresponding threshold values. When the data analyzed is a set of the multicellular signals of the biological interface apparatus of the present invention, the threshold may represent one or more of: a minimum modulation rate of one or more cells, a minimum number of cells with an acceptable modulation rate, or other multicellular signal parameter. In a preferred embodiment, one output of the analysis of step 22 is a measurement of patient consciousness and the threshold of step 23 is a minimum level of consciousness. If one or more comparisons to the associated one or more thresholds results in the threshold not being met, the system configuration plan is modified, and the patient training routine returns to step 20. In an alternative, at least one threshold value is set to force at least one modification of the system configuration plan, such as a threshold that cannot be met and is adjusted after the initial comparison of step 23 to a feasible level.

The modification to the system configuration plan may be automatically made by the system, manually accomplished by an operator, or both. The modification may require input from an operator, or multiple operators, and may invoke an integral permission routine of the system, as has been described in detail hereabove. The modification may create a change in the order of the steps of the first configuration plan. The modification may involve adding or deleting a step. The modification may result in the patient training routine to increase or decrease in time.

If the comparison of the one or more outputs of step 22 successfully compares to the one or more corresponding thresholds of step 23, step 24 is performed wherein a transfer function is generated to apply to the multicellular signals detected by the sensor of the present invention and produce the processed signals. Next sequential step 25 includes providing the patient with control of one or more controlled devices. The patient performs one or more tasks with the one or more controlled devices, and the performance of the patient control is measured. In a preferred embodiment, the measured performance is an error measurement of actual versus intended control. Performance data can be gathered with one or more sensors as well as one or more recording devices such as a video recorder and/or or a digital camera. Image processing techniques can be used to characterize the patient control of the controlled device. The characterization can be compared to a predetermined target, or it can be compared to a separate device movement pattern that the patient tries to mimic with the one or more controlled devices.

Next sequential step 26 includes comparing the measured performance of step 25 with one or more associated threshold values, such as the threshold values that can be modified by an operator of the system. If the measured performance is below the associated threshold value or values, the system configuration plan is modified and the next sequential step is initial step 20. If the measured performance is at or above the associated threshold value or values, the next sequential step 27 is performed. Step 27 includes building a transfer function, similar or dissimilar to the transfer function of step 24, the step 27 transfer function used by the system to produce the processed signals of the present invention. The next sequential step 28 includes initiating patient control of one or more controlled devices of the present invention. These controlled devices may be the same as, similar to, or different from the controlled devices of step 25.

Step 21 includes the building of a transfer function that is used to build a representation of the processed signals. The representation of the processed signal is a precursor to the processed signals used to control the controlled device. The representation of the processed signals may temporarily control the controlled device, a surrogate of the controlled device, or another device. In order to produce the processed signals, the processing unit includes a transfer function that is applied to the multicellular signals. The transfer function includes and/or is based upon one or more system configuration parameters that are generated and/or modified by the patient training routine. The representation of the processed signal is also produced with a transfer function that is applied to the multicellular signals, such as a transfer function that has parameters determined based on the temporal correlation of the first set of multicellular signals and the first set of states of the time varying stimulus. In an alternative, preferred embodiment, the representation of processed signals is modified with a bias toward a time varying stimulus that acts as a target for the patient's imagined movement. This improved control signal can be used as a motivator to the patient, and preferably has its improvement bias decrease as patient control performance increases.

Step 22 includes the patient training routine providing a set of states of a time varying stimulus and the representation of the processed signal whose transfer function is created in Step 21. While the patient receives, such as through viewing a visual display, listening to an audio signal, and/or feeling a tactile transducer, both the set of states of the time varying stimulus as well as the patient controlled feedback produced by the representation of processed signals, a next set of multicellular signals are recorded and stored. This next set is also correlated to the set of states of the time varying stimulus, such as a temporal correlation and/or other correlation described hereabove. The representation of the processed signal and/or the time varying stimulus, can be presented via the controlled device, a controlled device surrogate, or another device. The controlled device surrogate can be configured to be more complex than the intended controlled device, such that the patient is training with a more complicated device to improve eventual controlled device control. The surrogate device may have one or more differences, such as a larger value of one or more of: degrees of freedom; resolution; modes; discrete states; functions; boundary conditions; and combinations thereof. The boundary conditions of the surrogate can differ in one or more of: maximum distance; maximum velocity; maximum acceleration; maximum force; maximum torque; rotation; position; and combinations thereof.

The representation of the processed signals may be provided in a form similar to the time varying stimulus, or in a different form. In a preferred embodiment, the time varying stimulus is provided as an object on a visual display, and the representation of processed signals is the motion of a mechanical object such as a prosthetic limb. Both the time varying stimulus and the representation of processed signals can be provided in multiple forms selected from: visual; tactile; auditory; olfactory; gustatory; and electrical stimulation such as cortical stimulation. Both the time varying stimulus and/or the representation of processed signals can be provided as: moving object on screen; moving mechanical device such as a mechanical limb or wheelchair; moving part of patient's body such as via an exoskeleton device or FES device; changing audible signal such as a multi-frequency signal; and combinations thereof.

Referring back to FIG. 6, step 22 also includes the measuring of the performance of the representation of the processed signal as compared to the time varying stimulus. In a preferred embodiment, both the time varying stimulus and the representation of processed signals are presented as an object on a computer screen, and the performance is based on the ability of the patient to track the time varying stimulus object with the patient controlled object controlled by the representation of the processed signals. A performance measure value is determined and this value is compared to a predetermined success threshold value. If the performance measure value is at or above the success threshold value, the next step to be followed is Step 23 in which the patient training routine is completed and the current transfer function is subsequently used produce the processed signals to control the controlled device. If the performance measure value is below the success threshold value, the next step to be followed is a repeat of step 21 and its subsequent steps. In a preferred embodiment, the success threshold value is a system configuration parameter that is adjustable such as via a remote operator in which the permission routine is invoked to complete the change.

As stated above, if the performance meets or exceeds the threshold, the patient training routine proceeds to Step 23 wherein the processing unit utilizes the transfer function determined in the patient training routine to convert the multicellular signals received from the sensor of the present invention, and produces the processed signals to be transmitted to the controlled devices. In a preferred embodiment, a third set of states of time varying stimulus and a second representation of processed signals are used to create the transfer function. The second representation of processed signals is based on a second set of multicellular signal data previously recorded, or a combination of the first and second sets of multicellular signal data. In another preferred embodiment, the patient training routine must be performed at least one time in the use of the system, such as prior to the patient receiving full control of the controlled device. In an alternative embodiment, the patient training routine must be performed at least two times in the use of the system. In another preferred embodiment, the patient training routine must be successfully completed, such as when a performance parameter meets or exceeds a success threshold value, prior to the patient receiving full control of the controlled device. Full control of a controlled device is described in greater detail in reference to FIG. 3 herebelow.

In another preferred embodiment, the system of the present invention includes two controlled devices, and the patient training routine provides different feedback to the patient during the routine, such as different time varying stimulus or other feedback. Alternatively or additionally, the system may include a separate patient training routine for each controlled device. For the multiple controlled devices, a first set of states for a time varying stimulus will be provided to develop a transfer function for the first controlled device, and a second set of states for a time varying stimulus will be provided to develop a transfer function for the second controlled device. In a preferred embodiment, the first controlled device is a prosthetic or exoskeleton driven arm, and the second controlled device is a prosthetic or exoskeleton driven leg. In another preferred embodiment, the first controlled device is a prosthetic or exoskeleton driven arm, and the second controlled device is a vehicle such as a wheelchair.

As stated above, the patient training routine can be used to generate one or more system configuration parameters used by the processing unit to develop a transfer function to produce processed signals. The selection of cells for processing as well as criteria for selecting cells may be generated. A signal processing parameter can be generated such as a coefficient modifying one or more of the following: amplification, filtering, sorting, conditioning, translating, interpreting, encoding, decoding, combining, extracting, sampling, multiplexing, analog to digital converting, digital to analog converting, mathematically transforming; and combinations thereof. A control signal transfer function parameter, such as a coefficient value; algorithm; methodology; mathematical equation; and combinations of those may be generation. A calibration parameter such as calibration frequency and/or a controlled device parameter such as a controlled device parameter boundary limit may be generated. Other system configuration parameters that can be generated by the patient training routine include but are not limited to: acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signal to patient; calibration parameter such as calibration duration and calibration frequency; controlled device parameter such as controlled device mode; alarm or alert threshold; success threshold; and combinations thereof.

In another preferred embodiment, the patient training routine of the present invention adapts over time. Each time the patient training routine is invoked, a patient training event, one or more changes may be made for the next patient training event. A change may be caused by a measurement of performance, such as controlled device control performance. A control at or above a threshold, measured as has been described in detail hereabove, may result in a subsequent patient training routine of a shorter duration. Alternatively, performance below a similar threshold may result in a longer patient training routine, and/or a modified patient training routine. The patient training routine may adapt based on a multicellular signal change, such as the death of one or more cells previously providing cellular signals. The patient training routine may adapt due to a change in a patient parameter, such as a change due to a change in patience consciousness level. In the circumstance wherein patience consciousness falls below a threshold, a patient training routine may adapt within the routine itself—such as to repeat a step, or delay a step until consciousness is at a higher level. Patient consciousness may be measured using the multicellular signals of the sensor of the present invention, or another sensor of the system such as an EEG or LFP sensor.

In another preferred embodiment, the patient training routine automatically adapts, such as by being triggered by a system-monitored parameter crossing a threshold. Alternatively, the routine may adapt based on an operator input.

Routines may adapt within a single patient training event, or between patient training events. Routines may adapt based on a measure of performance in a previous patient training routine event, or based on a comparative difference between two patient training events.

Numerous methods are provided in the multiple embodiments of the disclosed invention. A preferred method embodiment includes providing an automated patient training routine for a biological interface apparatus that provides a visual representation of a human figure to the patient. The visual representation includes multiple body movements that are provided such that the patient can imagine a similar movement. The biological interface system is for collecting multicellular signals emanating from one or more living cells of a patient and for transmitting processed signals to control a device. The biological interface system comprises: a sensor for detecting the multicellular signals, the sensor comprising a plurality of electrodes to allow for detection of the multicellular signals; a processing unit for receiving the multicellular signals from the sensor, for processing the multicellular signals to produce processed signals, and for transmitting the processed signals; a controlled device for receiving the processed signals; and a patient training routine for generating one or more system configuration parameters.

It should be understood that numerous other configurations of the systems, devices and methods described herein could be employed without departing from the spirit or scope of this application. It should be understood that the system includes multiple functional components, such as a sensor for detecting multicellular signals, a processing unit for processing the multicellular signals to produce processed signals, and the controlled device that is controlled by the processed signals. Different from the logical components are physical or discrete components, which may include a portion of a logical component, an entire logical component and combinations of portions of logical components and entire logical components. These discrete components may communicate or transfer information to or from each other, or communicate with devices outside the system. In each system, physical wires, such as electrical wires or optical fibers, can be used to transfer information between discrete components, or wireless communication means can be utilized. Each physical cable can be permanently attached to a discrete component, or can include attachment means to allow attachment and potentially allow, but not necessarily permit, detachment. Physical cables can be permanently attached at one end, and include attachment means at the other.

The sensors of the systems of this application can take various forms, including multiple discrete component forms, such as multiple penetrating arrays that can be placed at different locations within the body of a patient. The processing unit of the systems of this application can also be contained in a single discrete component or multiple discrete components, such as a system with one portion of the processing unit implanted in the patient, and a separate portion of the processing unit external to the body of the patient. The sensors and other system components may be utilized for short term applications, such as applications less than twenty four hours, sub-chronic applications such as applications less than thirty days, and chronic applications. Processing units may include various signal conditioning elements such as amplifiers, filters, signal multiplexing circuitry, signal transformation circuitry and numerous other signal processing elements. In a preferred embodiment, an integrated spike sorting function is included. The processing units performs various signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controllable device. The processing unit utilizes numerous algorithms, mathematical methods and software techniques to create the desired control signal. The processing unit may utilize neural net software routines to map cellular signals into desired device control signals. Individual cellular signals may be assigned to a specific use in the system. The specific use may be determined by having the patient attempt an imagined movement or other imagined state. For most applications, it is preferred that that the cellular signals be under the voluntary control of the patient. The processing unit may mathematically combine various cellular signals to create a processed signal for device control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A biological interface system comprising:
a sensor comprising a plurality of electrodes for detecting multicellular signals emanating from two or more living cells of a patient;
a processing unit configured to receive the multicellular signals from the sensor, process the multicellular signals to produce a processed signal, and transmit the processed signal to a controlled device;
the controlled device for receiving the processed signal; and
an integrated system troubleshooting routine performed to improve system performance comprising modifying one or more system configuration parameters used by the processing unit to produce the processed signal, wherein the integrated system troubleshooting routine provides a first visual representation of a human figure to the patient,
wherein the system troubleshooting routine automatically adapts from a first patient training routine event to a second patient training routine event based on a comparative difference between the first patient training routine event and the second patient training routine event
wherein the system troubleshooting routine provides a second visual representation of a human figure and
wherein the first visual representation is provided simultaneously with the second visual representation to improve the quality of the system configuration parameters generated.

2. The system of claim 1, further comprising a remote access routine.

3. The system of claim 2, further comprising an internet connection such that a remote technician can send and/or receive data from said system.

4. The system of claim 1, wherein the system troubleshooting routine is embedded in a component of the system at a location remote from the patient.

5. The system of claim 1, wherein the first visual representation and the second visual representation include multiple human body movements.

6. The system of claim 5, wherein the multiple human body movements are provided for the patient to imagine said movement.

7. The system of claim 6, wherein the system stores a set of multicellular signals while the patient imagines said movements.

8. The system of claim 1, wherein the first visual representation and the second visual representation include a photographic series of images of a human being.

9. The system of claim 1, wherein the first visual representation and the second visual representation are an animated series of images of a human being.

* * * * *